(12) United States Patent
Bustamante et al.

(10) Patent No.: US 11,819,729 B2
(45) Date of Patent: Nov. 21, 2023

(54) ARMCHAIR FOR PHYSICAL THERAPY WITH IOT FUNCTIONALITY

(71) Applicant: BT5 Technologies, LLC, Katy, TX (US)

(72) Inventors: Luis Bustamante, The Woodlands, TX (US); Daniella Bustamante, The Woodlands, TX (US)

(*) Notice: Subject to any disclaimer, the term of this patent is extended or adjusted under 35 U.S.C. 154(b) by 566 days.

(21) Appl. No.: 17/093,526

(22) Filed: Nov. 9, 2020

(65) Prior Publication Data

US 2021/0138293 A1 May 13, 2021

Related U.S. Application Data

(60) Provisional application No. 62/933,426, filed on Nov. 9, 2019.

(51) Int. Cl.
| | | |
|---|---|---|
| A63B 21/00 | (2006.01) | |
| A63B 21/04 | (2006.01) | |
| A47C 27/00 | (2006.01) | |
| A47C 7/62 | (2006.01) | |
| A63B 21/08 | (2006.01) | |
| A63B 21/055 | (2006.01) | |
| A61B 5/00 | (2006.01) | |

(52) U.S. Cl.
CPC ............ *A63B 21/4027* (2015.10); *A47C 7/62* (2013.01); *A61B 5/6891* (2013.01); *A63B 21/0442* (2013.01); *A63B 21/0552* (2013.01); *A63B 21/08* (2013.01)

(58) Field of Classification Search
CPC ............ A63B 21/1609; A63B 21/4027; A63B 21/0442; A63B 21/0552; A63B 21/08; A47C 9/002; A47C 7/62; A61B 5/6891
See application file for complete search history.

(56) References Cited

U.S. PATENT DOCUMENTS

| | | | | |
|---|---|---|---|---|
| 4,913,423 A | * | 4/1990 | Farran | A63B 21/154 482/904 |
| 4,921,247 A | * | 5/1990 | Sterling | A63B 21/4035 482/130 |
| 5,605,526 A | * | 2/1997 | Hatfield | A47C 9/002 482/142 |
| 6,159,133 A | * | 12/2000 | Shugg | A63B 21/4007 482/121 |

(Continued)

*Primary Examiner* — Shin H Kim
(74) *Attorney, Agent, or Firm* — Joseph P. Aiena

(57) ABSTRACT

There is provided an IoT therapy armchair, in unitary form, with a chassis having a back section, a pair of side sections connected to the back section with an armrest on a top surface of each side section with the back section and pair of sides defining a seating area. A front leg support section extends downward from and below the seating area and connects each of the side sections. A plurality of pressure hangers fastened to the chassis, each of which are capable of receiving an exercise accessory, each connected to a respective pressure transducer, that measures an amount of pressure applied to each of the plurality of pressure hangers. The amount of pressure applied and health sensors are communicated as an output signal to a computing device that create statistics, reports of health conditions, early warnings, alarms, and communicates online and provides interactive therapy guidance to users.

11 Claims, 25 Drawing Sheets

(56) References Cited

U.S. PATENT DOCUMENTS

| | | | |
|---|---|---|---|
| 8,696,531 B1* | 4/2014 | Spiller | A47C 9/002 |
| | | | 482/904 |
| 11,612,781 B1* | 3/2023 | Eoff | A47C 1/022 |
| | | | 482/130 |
| 2004/0124680 A1* | 7/2004 | Harris | A47C 7/425 |
| | | | 297/284.5 |
| 2007/0099780 A1* | 5/2007 | Bowser | A63B 21/00043 |
| | | | 482/148 |
| 2008/0153680 A1* | 6/2008 | Bendavid | A63B 21/1609 |
| | | | 482/122 |
| 2009/0152915 A1* | 6/2009 | Krasna | A47C 7/624 |
| | | | 297/217.3 |
| 2009/0163336 A1* | 6/2009 | Mueller | A63B 21/1609 |
| | | | 482/129 |
| 2009/0270231 A1* | 10/2009 | Hall | A63B 23/10 |
| | | | 482/79 |
| 2017/0319891 A1* | 11/2017 | Holt | A63B 21/0442 |
| 2018/0027987 A1* | 2/2018 | Calhoun | A47C 7/62 |
| 2018/0339181 A1* | 11/2018 | Weisz | A63B 21/1609 |
| 2020/0046128 A1* | 2/2020 | Sramek | A47C 1/02 |
| 2021/0138293 A1* | 5/2021 | Bustamante | A63B 21/08 |
| 2022/0161094 A1* | 5/2022 | Higginson | A63B 22/0087 |

* cited by examiner

210

220

230

235

ARMCHAIR FOR PHYSICAL THERAPY WITH IOT FUNCTIONALITY

CROSS REFERENCE TO RELATED APPLICATIONS

This application claims the benefit of and priority to U.S. Provisional Patent Application Ser. No. 62/933,426 filed on Nov. 9, 2019 and incorporated by reference herein in its entirety.

FIELD OF THE INVENTION

The present invention generally relates to physical therapy furniture. More particularly, the present invention relates to an armchair with a heavy-duty chassis that allows users to do physical exercises with accessories that are connected to pressure transducers which send signals to the cloud via a computer and a software application.

BACKGROUND

The furniture used to do physical therapy is generally used in specialized therapy centers where experts direct and accompany the patient in their exercises. However, patients may desire to perform the exercises at a different location or at home when convenient.

SUMMARY OF THE INVENTION

The present invention is a therapy chair that is used to increase the strength of a user's upper and lower extremity (UL/LE) musculature, to maintain functional mobility and promote a healthy lifestyle.

The armchair of this invention is also used to maintain strength (vs increasing strength), to reduce the progressive decline of strength/function during the aging process, or to improve muscular endurance. With this present invention, armchair for therapy with IoT capabilities, a unique generation of healthcare furniture comes into existence.

Some of the main components of the armchair of the present invention is a single heavy-duty chassis comprising different hangers, handles, stability weights, leveler stabilizers, a step-stand, pressure measuring transducers (or sensors), health sensors, storage sections, a touch-screen computer with speakers, IoT connectivity, a customized software package for therapy and mechanical accessories and power supply connector.

The present invention is an IoT therapy chair, in unitary form, with a chassis having a back section, a pair of side sections connected to the back section with an armrest on a top surface of each side section with the back section and pair of sides defining a seating area. A front leg support section extends downward from and below the seating area and connects each of the side sections. A plurality of pressure hangers fastened to the chassis, each of which are capable of receiving an exercise accessory, and each of the pressure hangers connected to a respective pressure transducer that measures an amount of pressure applied to each of the plurality of pressure hangers when the exercise accessory (such as exercise bands) is used by an individual. The amount of pressure applied to the pressure hangers is communicated as an output signal to a computing device. This allows users to do physical exercises with accessories that are connected to pressure transducers which send signals to the cloud via a computer and a software application.

The pressure transducer converts the amount of pressure applied to each of the plurality of pressure hangers into a logic signal for each. The logic signal is routed to a multiplexer to read the logic signal of each of the plurality of pressure hangers and then a multiplexer converts all of the logic signals to a single output signal. This single output signal is communicated to a computing device which includes access to numerous healthcare features and monitoring, along with interactive online feedback.

This armchair of the present invention provides convenience for users who want to recover from an injury or stay in good physical condition. It allows them to do therapy more easily, for instance, while relaxing and watching TV at home. This invention also provides the possibility to obtain professional advice or assisted services through online connectivity at what maybe more affordable rates than visiting a therapy center without spending time on travel to that type of facilities, and perhaps, without having to sweat so much doing the exercises at those centers. Like any new exercise program, certain users may need a doctor's approval to begin an exercise program based on their overall health or pre-existing conditions. Users can use interactive or online professional assisted services to do therapy or other exercises.

In an embodiment, the armchair for therapy of the present invention includes the armchair chassis having a base section with a weight support section connected to the base section, a seat member section connected to the base section, first and second arm rest section connected to the base section, and a backrest section connected to the base section.

In another embodiment, the armchair for therapy includes the armchair chassis where the base section is a U-shaped piece having a pair of parallel side members connected by a front member between the pair of parallel side members. Each of the pair of parallel side members have an inward turned portion at an open end of the U-shaped piece and the inward turned portion creates a corner to align with the backrest section. A cross support member is fixed between the pair of parallel side members.

In another embodiment, the armchair for therapy includes where the base section has a weight support section having an H-shaped frame piece with two parallel members and a cross member located between and connecting the two parallel members. A guide pin for receiving weights extends upward from the cross member. The weight support member piece is fixed inside the base section between the front member and the cross support member of the base section.

In an embodiment, the chassis for the armchair for therapy of the present invention includes the seat member section having a front, a back and four vertical pieces of equal height with two of the vertical pieces located in the front of the seat member section and two of the vertical pieces located in the back of the seat member section. The front two of the vertical pieces are secured by a cross beam and each of the two front vertical pieces are fixed to a first and a second seat inner beam. The back two of the vertical pieces are connected by a seat back beam piece and each of the first and second seat inner beams are connected to the seat back beam piece. The seatback beam piece is longer than the cross beam piece securing the front two of the vertical pieces and the two front vertical pieces of the seat member section are positioned and fixed along a top surface of the front member of the base section, and the two vertical back pieces are positioned and fixed to the parallel side members of the base section.

The armchair for therapy of the present invention includes an embodiment where the first and second arm rest sections of the chassis are an L-shaped right angle piece. The first and second arm rest sections each have a pair of vertical and parallel members, with the vertical and parallel members positioned on the front member of the base section of the chassis. The vertical and parallel members each intersect and connect with a top pair of parallel members parallel to the base section. The top pair of parallel members have a cross spacer piece fixed between the top pair of parallel members at a front end of each of the top pair of parallel members.

In an embodiment, the armchair for therapy has a chassis with a backrest section which includes two upright parallel members on a right side and two upright parallel members on a left side. The backrest section has a first cross member positioned between the two upright parallel members on the right side and a second cross member positioned between the two upright parallel members on the left side. The back section includes a pair of top members perpendicular to the two upright parallel members on the right side and perpendicular to the two upright members on the left side with the pair of top members connected to a top end of each of the four upright parallel members. The top members are parallel to the base. The four upright parallel members are fastened on the base section parallel side members with the back two upright parallel members aligned with the back corners of the base section. The backrest section has a cross beam fixed between two front upright parallel members, with the first arm rest section and the second arm rest section connected to the cross beam to secure the first arm rest section and the second arm rest section to the backrest section.

DETAILED DESCRIPTION OF DRAWINGS

Figure 1:
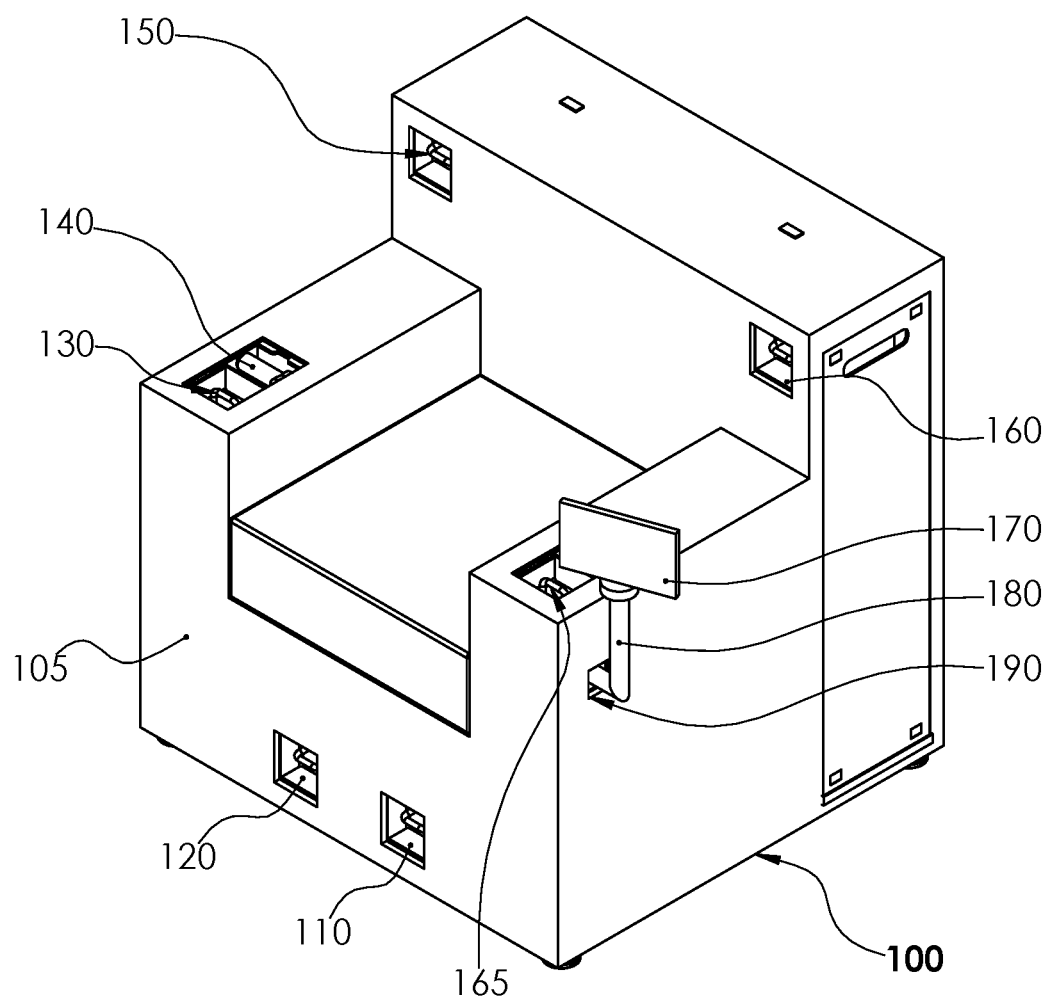
FIG. 1 is a frontal isometric illustration of the present invention.
Figure 2A:
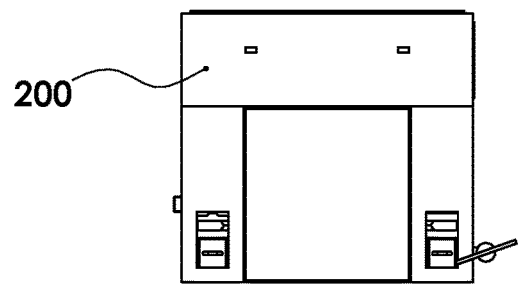
FIGS. 2A, 2B, 2C, 2D and 2E are illustrations of the present invention in top, right, front, left and rear views, respectively.
Figure 2B:
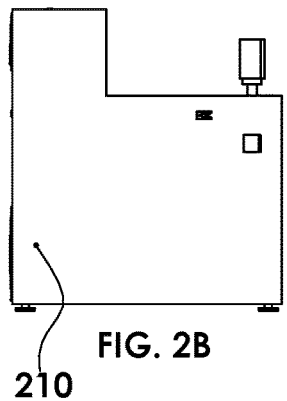
Figure 2C:
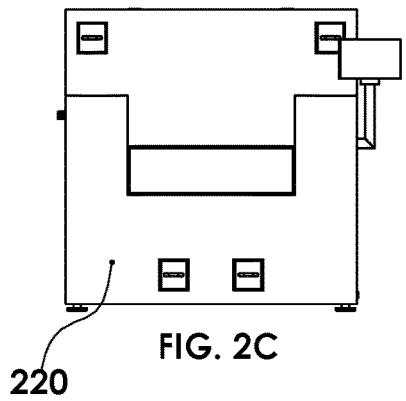
Figure 2D:
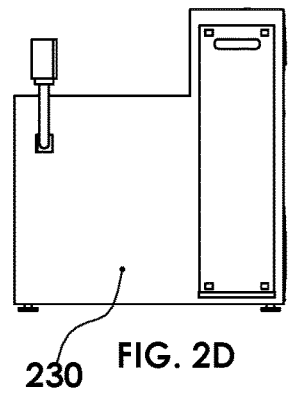
Figure 2E:
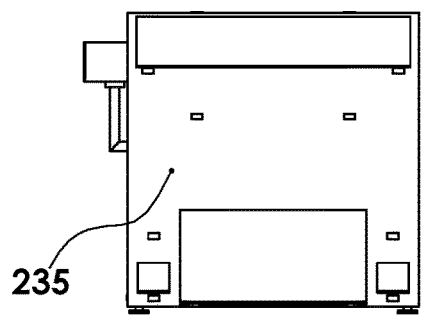
Figure 3A:
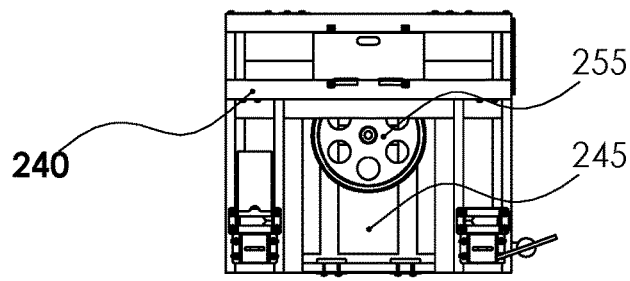
FIGS. 3A, 3B, 3C, 3D and 3E are illustrations of the chassis of the chair of the present invention in top, right, front, left and rear views, respectively.
Figure 3B:
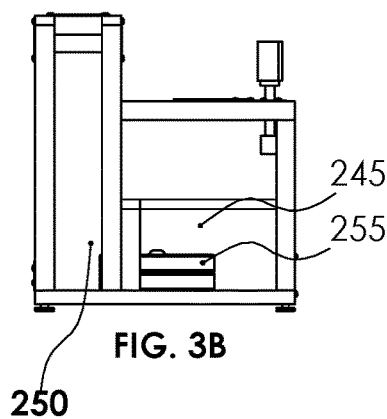
Figure 3C:
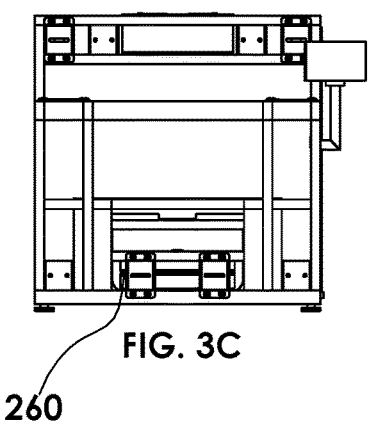
Figure 3D:
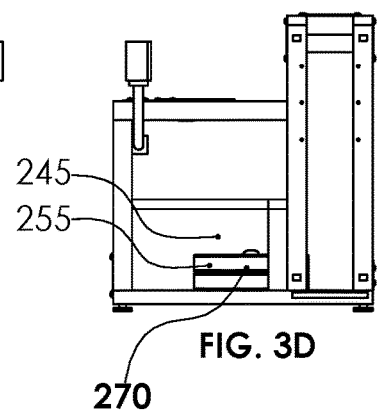
Figure 3E:
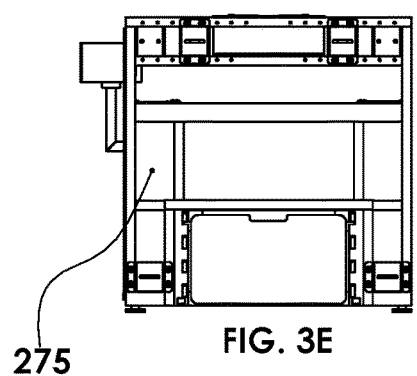

Referring to FIG. 1, there is shown the IoT armchair for physical therapy 100 of this invention. The chair includes a back and two upright side arm sections which define a seating area positioned below the top surface of the arm sections. The front of the chair includes a lower frontal section below the seating area, connected to the two upright side arm sections, creating a unitary chair frame. The Figure shows the sleeve cover 105 manufactured with an ergonomic material for therapy purposes with a special heavy-duty chassis that contains different accessories and devices. The armchair contains, among others, multiple pressure hangers, such as, six (6) pressure hangers in the front 110, 120, 130, 150, 160 and 165 and four (4) hangers in the rear side that will be explained in detail in the following Figures. Each of the armrests section includes two handles 140 in order to provide the user stability while sitting and doing an exercise for the legs. The armchair includes a touch-screen computer 170 that is connected mechanically to the chair by means of, but not limited to, a rotative bracket 180 and installed in a plug-in connector 190 located in the right and left sides of this invention, as preferred by the user. The computer is connected to the armchair of this invention through a bracket that can be fixed to the armchair, or that can rotate on a mobile connector located on each side of the armchair. In this way when the user is not using the armchair, a user can rotate the computer bracket on the side of the armchair and hide the computer to maintain a clean visual presentation of the chair from the back, for example, to a better presentation when the armchair is located in the family room.

FIG. 2A thru 2E are illustrations of the present invention showing the top 200, right 210, front 220, left 230 and rear 235 views, respectively.

FIG. 3A thru 3E are illustrations of the chassis/frame of the present invention showing top 240, right 250, front 260, left 270 and rear 275 views, respectively, to provide a view of the internal weighted area 245 and weight(s) 255 and the alignment of individual internal frame pieces connected to each other to form the chair.

Figure 4:
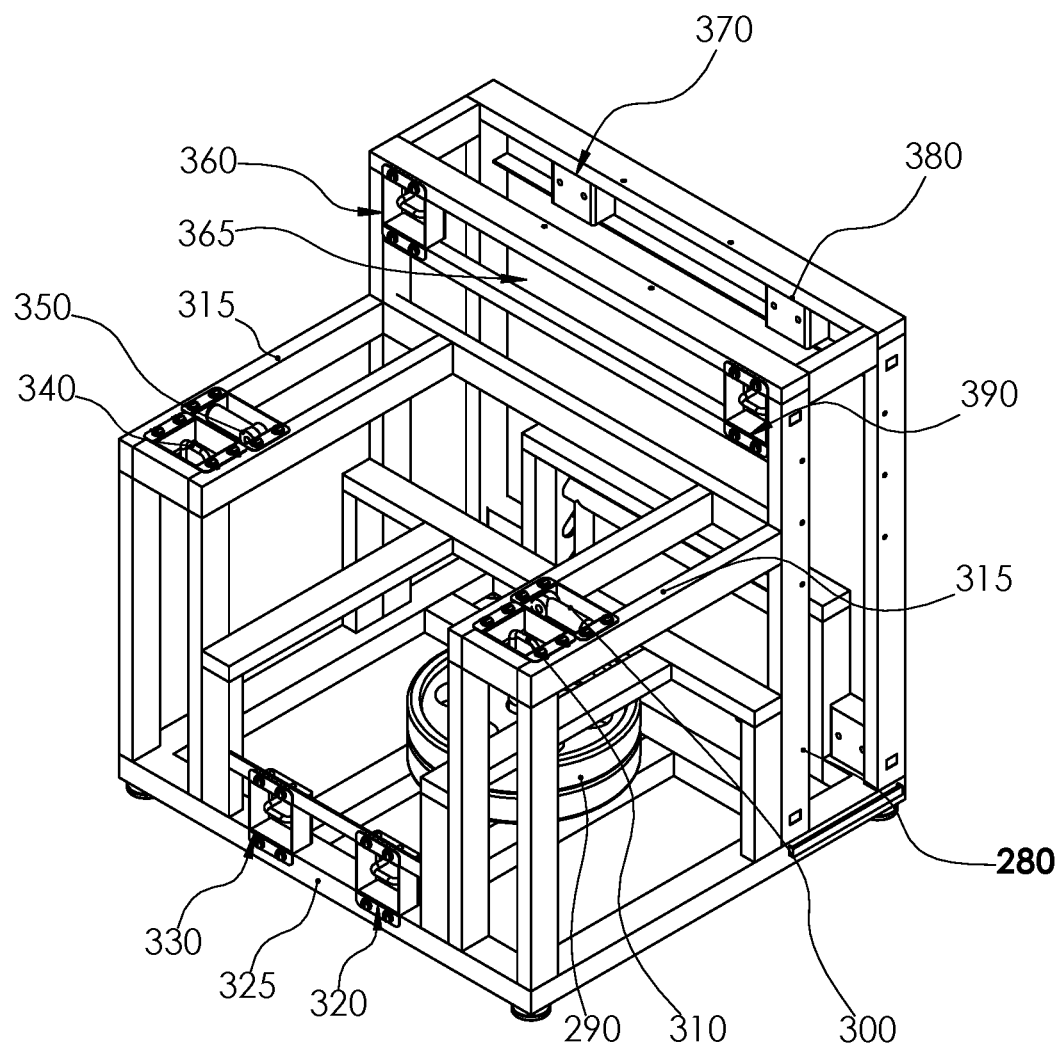
FIG. 4 is a right frontal isometric illustration of the chassis of the present invention.

FIG. 4 is a frontal isometric illustration of the chassis 280 of the present invention. The chassis 280 is built of different materials including, but not limited to, metal, plastic and wood that provide strength and heavy-duty stability for the use of the present invention. The heavy-duty chassis includes, but is not limited to, different accessories hangers 310 and 340 in the armrest sections 315, hangers 320 and 330 in the front lower section 325, handles 300 and 350 in the armrest sections 315 to provide mechanical support to the user, upper front hangers 360 and 390 located in the backrest 365, and rear upper hangers 370 and 380.

Figure 5:
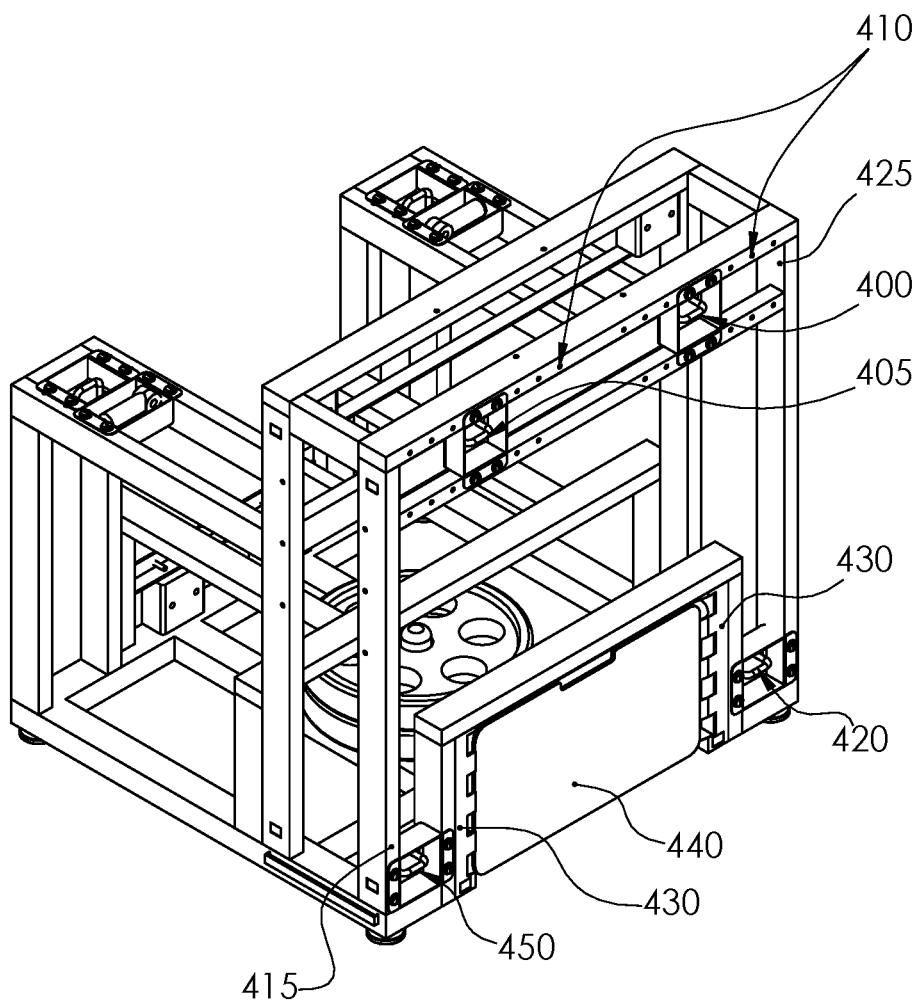
FIG. 5 is a left rear isometric illustration of the chassis of the present invention.

FIG. 5 is an isometric illustration of the heavy-duty chassis in the left rear view of the present invention. As shown, there are two hangers 400 and 405 in the upper rear side 425 that can be moved and adjusted laterally in a selection of numerous different positions 410 (illustrated by mechanical supports with defined holes) to fit user requirements and then fix the hangers 400 and 405 in the position desired. In the low rear side 415, two additional hangers 420 and 450 are shown. Additionally, the present invention allocates a removable stand step 440 on the low back side that can be adjusted in four different positions in the rail support 430. This stand step 440 is built of a resistant material including, but not limited to, metal, plastic and wood that provides strength and stability for the use of the present invention.

Figure 6:
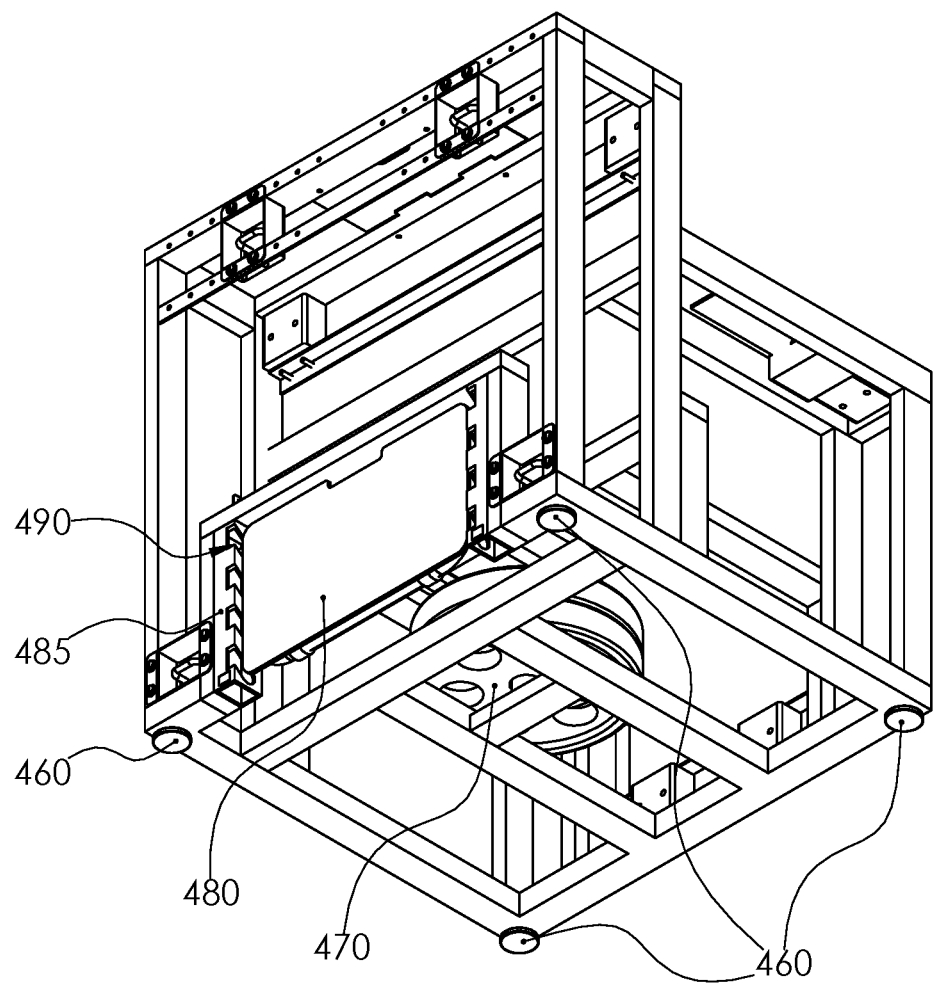
FIG. 6 is a bottom right isometric illustration of the chassis of the present invention.

With reference to FIG. 6, there is an isometric bottom rear view of the heavy-duty chassis of the present invention. The stand step 480 is fixed in the higher position 490 of the rail support 485 when stored. The weight(s) 470 provides the chair with greater stability and firmness to the floor when the user is exercising with the chair in a standing position. The objective of placing weights 470 on the chassis of the armchair is to prevent the armchair from moving when the user is standing and using bands attached to the armchair, which may create forces attempting to move the armchair from its fixed position. Other stability options are to fix the base of the chair to the floor or other fixed areas by means of mechanical connectors.

The access to install or remove the weights 470 is, but not limited to, by the step stand cavity section located in the rear side, behind/inside stand step 480, or by removing the seat cushion in the front side. The armchair is equipped with four foot levelers 460 to level up and adjust the height above the floor, adapting to the requirements of each user.

Figure 7A:
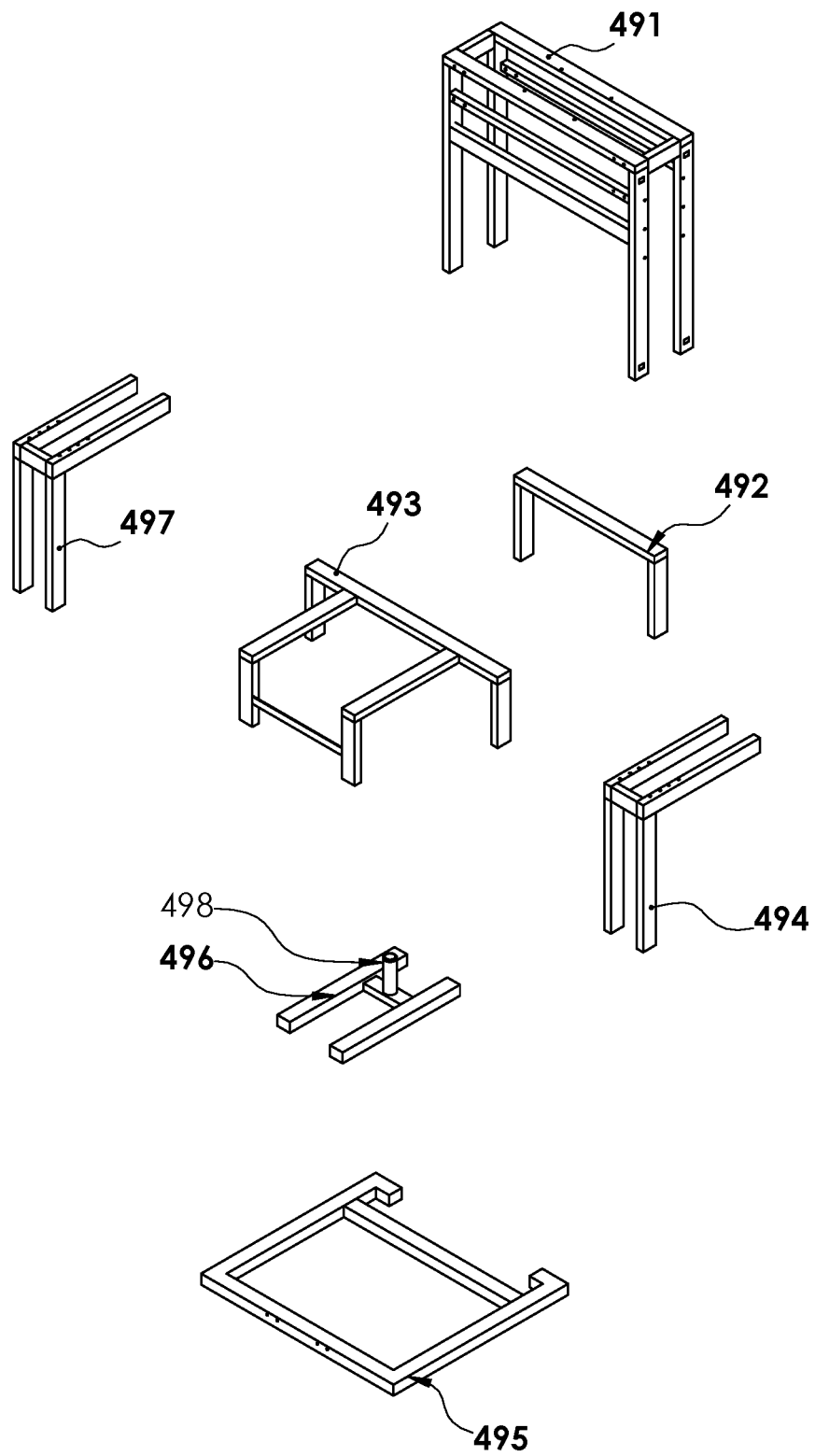
FIG. 7A is an illustration in an exploded view of the sections of the chassis of the present invention.

In FIG. 7A, there is an illustration of the exploded view of the heavy-duty chassis of the present invention. This chassis is built of a base section 495, with a weight support section 496 that includes a guide pin 498, a first (right) armrest section 497, a second (left) armrest section 494, a seat member section 493, a stand-step hanger section 492 and the backrest section 491 of the armchair of this invention.

Figure 7B:
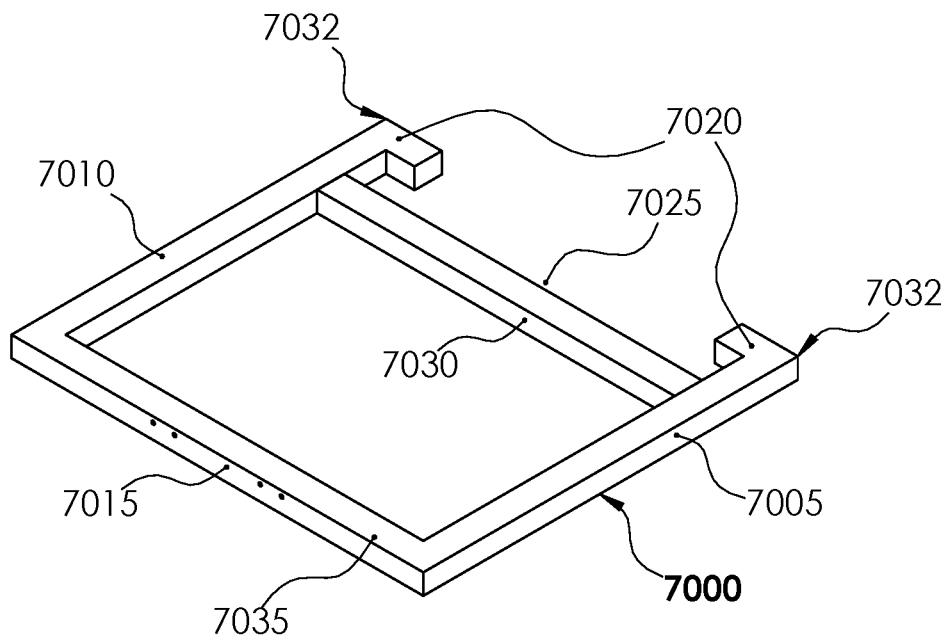
FIG. 7B is an illustration in an isometric view of the chassis base section of the present invention.

In FIG. 7B the base section 7000, which is a generally U-shaped piece formed from a pair of parallel side members 7005, 7010 connected by a front member 7015 between and preferably, perpendicular to the parallel side members 7005 and 7010 although other configurations are within the scope of the invention, such as curves or other shapes. Each of the parallel side members 7005 and 7010 have an inward turned portion 7020 at the open end 7025 of the U-shaped base piece 7000, thereby creating, forming, and generating the corners 7032 which are aligned with and receive the backrest section (FIG. 7F, 7220) in the chassis assemble. A cross-support member 7030 is fixed and located between the parallel side members 7005 and 7010. Over the top surface 7035 of the base section 7000 are assembled the rest of the sections of FIG. 7A that compose the chassis of the armchair of the present invention.

Figure 7C:
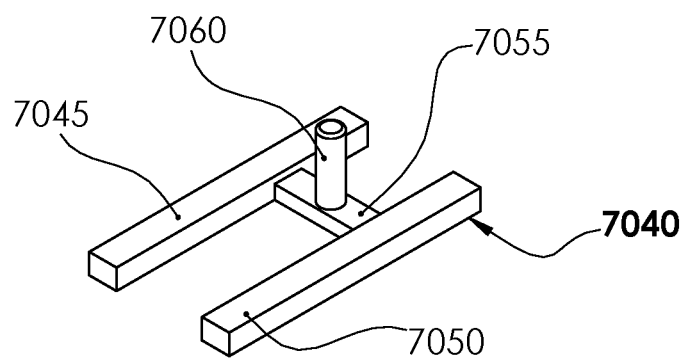
FIG. 7C is an illustration in an isometric view of the chassis weight support section of the present invention.

In FIG. 7C there is shown the weight support section 7040 that is an H-shaped frame piece with two parallel members 7045 and 7050 and a smaller cross member 7055 located between and connecting the two parallel members 7045 and 7050 of the weight support section 7040. Extending upward from the smaller cross member 7055 is a guide pin 7060, for receiving weights. The weight support piece 7040 is positioned and fixed inside the base 7000 between the front member 7015 and the cross-support member 7030 of the base section 7000 of FIG. 7B.

Figure 7D:
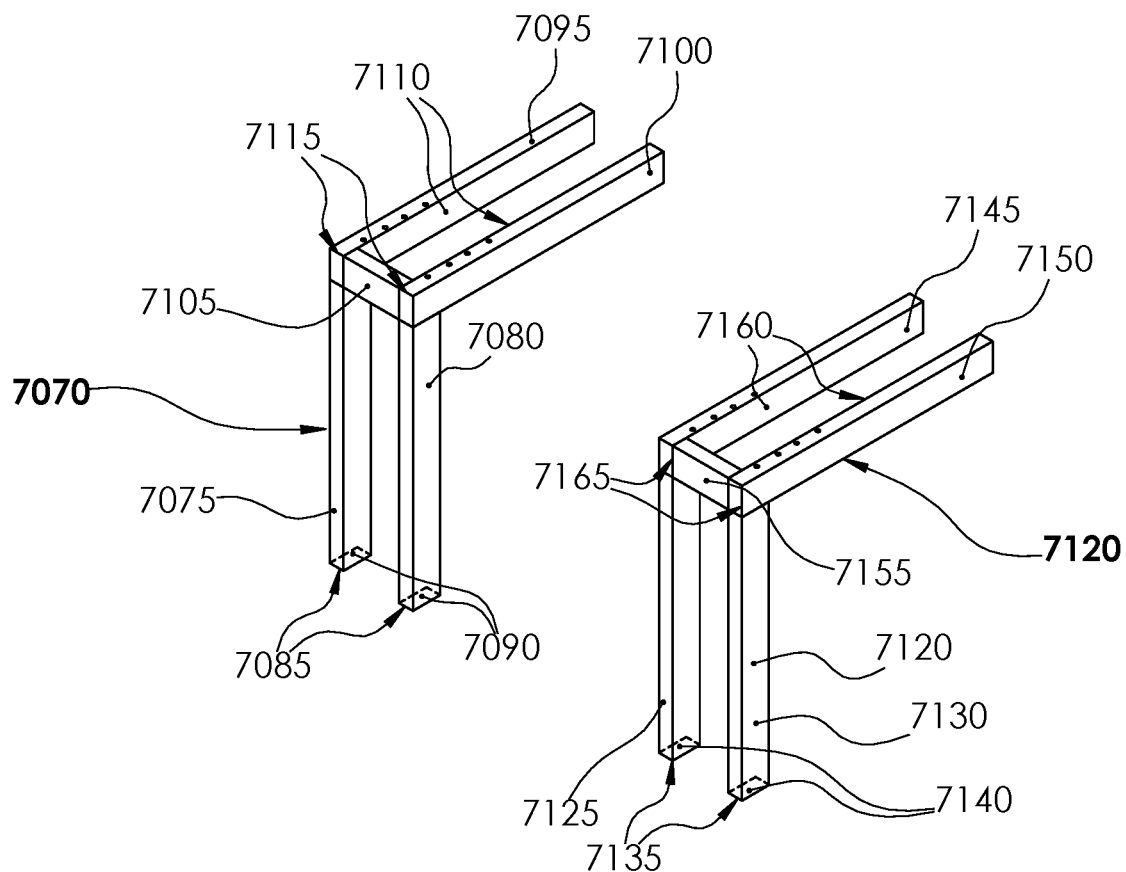
FIG. 7D is an illustration in an isometric view of the chassis left and right armrest sections of the present invention.

In FIG. 7D, there is shown the right arm rest section 7070 and the left arm rest section 7120 structures. The right arm rest section 7070 and left arm rest section 7120 are each L-shaped right-angle pieces which each have a pair of upwardly extending vertical and parallel members 7075, 7080 and 7125, 7130 which are perpendicular to the floor and base section. The bottom ends 7085 and 7135 and bottom surfaces 7090 and 7140 of these upwardly extending parallel members 7075, 7080, 7125, 7130 are fixed and positioned on the top surface 7035 of the front member 7015 of the base section 7000, (shown in the FIG. 7B), when the chassis is assembled. The upwardly extending members 7075 and 7080 of the right arm rests section 7070 and 7125, and 7130 of the left arm rests section 7120, each intersect and connect with a pair of parallel members 7095, 7100 in the right arm rest section 7070 and 7145, 7150 in the left arm rest section 7120, which are also parallel to the floor plane in order to form the L-shaped right angle pieces. The top pair of parallel members 7095, 7100 of the right arm rest section 7070 have a cross spacer piece 7105 fixed between them at the inside surface 7110 of the front ends 7115 of each of the parallel members 7095, 7100 to maintain stability and positioning of the top parallel members 7095, 7100. Similarly, the top pair of parallel members 7145, 7150 of the left arm rest section 7120 have a cross spacer piece 7155 fixed between them for positioning and stability at the inside surfaces 7160 of the front ends 7165 of the top pair of parallel members 7145 and 7150. The cross-spacer pieces 7105 and 7155, provide the positioning and space between the top pair of parallel members 7095, 7100 and 7145, 7150 to receive the hangers 310 and 340 and also the arm rest handle boxes 300 and 350, shown in FIG. 4.

Figure 7E:
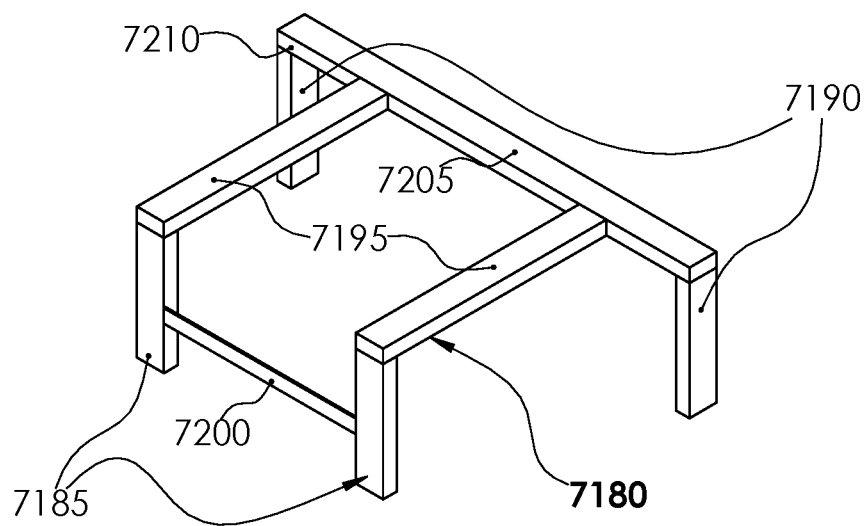
FIG. 7E is an illustration in an isometric view of the chassis seat section of the present invention.

In FIG. 7E, there is shown the seat section. The seat section 7180 has four upwardly extending vertical pieces of equal height, two in the front 7185 and two in the back 7190. The two front pieces 7185 are each fixed and connected to a respective first and second seat inner beam 7195 at a right angle. A cross beam 7200 is fastened and secured between the two front pieces 7185 to maintain positioning and stability and to receive the brackets for the hangers 320 and 330, shown in FIG. 4 discussed previously. The two back upwardly extending pieces 7190 are fixed and connected to a seat back beam piece 7205 which is parallel to the plane of the floor. The seat back piece 7205 is longer than the cross beam 7200 positioned between the two front pieces 7185. Each of the seat inner beams 7195 is connected to the seat back beam 7205 on the side surface 7210 of the seat back beam 7205. In assembly, the two front pieces 7185 of the seat section are positioned and fixed preferably along the top surface 7035 of the front member 7015 of the base section 7000, and the two back pieces 7190 are positioned and fixed to the parallel side members 7005, 7010 of the base section 7000, shown in FIG. 7B.

Figure 7F:
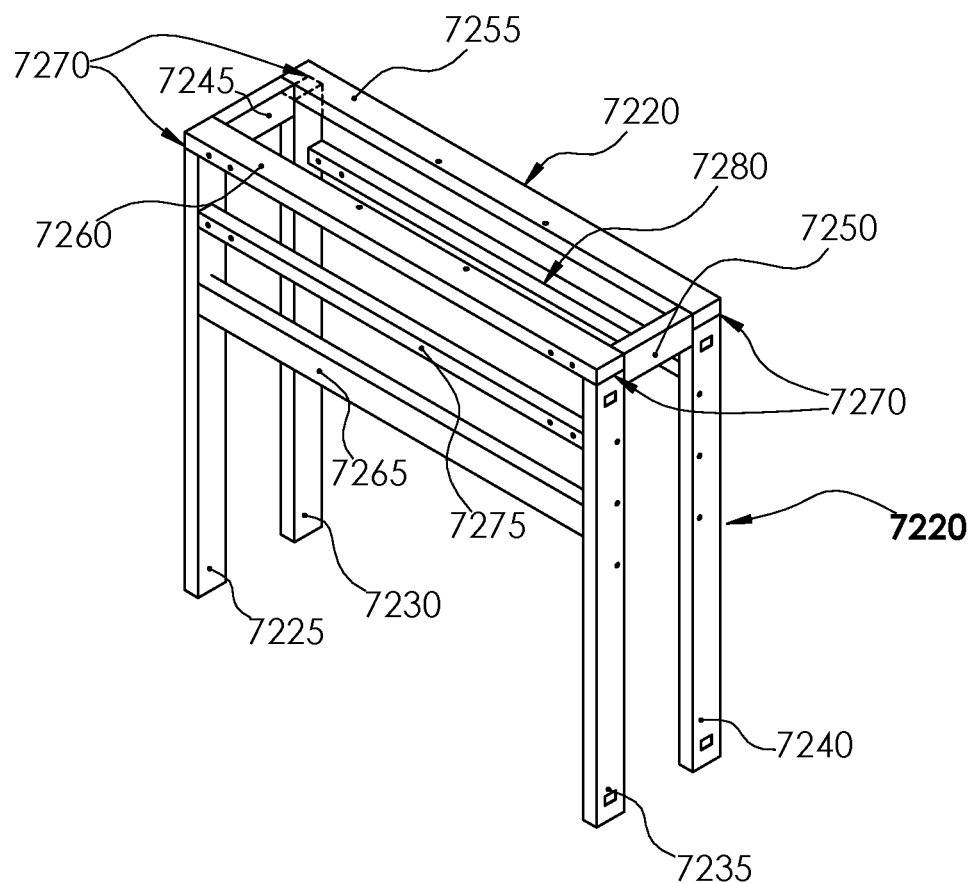
FIG. 7F is an illustration in an isometric view of the chassis backrest section of the present invention.

FIG. 7F shows the backrest section 7220 which has two upright parallel members 7225, 7230, on the right side and two upright parallel members 7235, 7240, on the left side (for a total of four) with a cross member 7245, 7250 connecting and positioning them on each side, and a pair of top members 7255, 7260, perpendicular to the upright members and connected to the top ends 7270, of the upright members 7225, 7230 and 7235, 7240. The four upright parallel members 7225, 7230 and 7235, 7240 are fastened on the parallel side members 7005, 7010 of the base section 7000 (in FIG. 7B), with the back two upright parallel members 7230 and 7240, aligned with the back corners 7032 of the base section 7000, of FIG. 7B. The backrest section 7220 also includes a cross beam 7265 fixed between the two front upright parallel members 7225, 7235. The right arm rest section 7070 and left arm rest section 7120 (FIG. 7D) are fixed and connected to this cross beam 7265 to secure them to the backrest section 7220. A bracket 7275 is also fixed between the two front upright parallel members 7225, 7235, for receiving the hangers 360 and 390 (shown in FIG. 4) that are mounted between the bracket 7275 and the front top member 7260. Similarly, a bracket 7280 is fixed between the two back upright parallel members 7230, 7240, to receive the hangers 400 (shown in FIG. 5), which can have their position adjusted along the length of the bracket 7280.

Figure 7G:
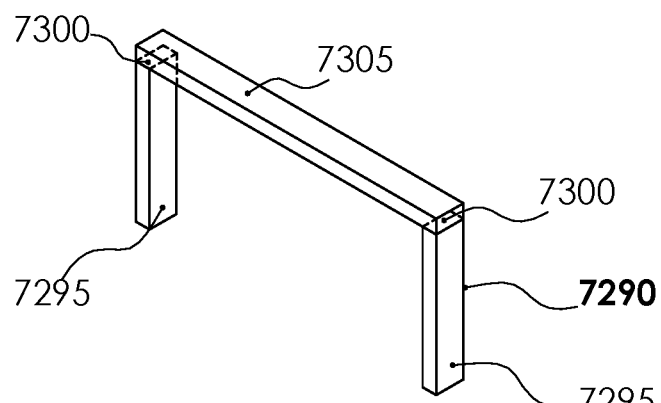
FIG. 7G is an illustration in an isometric view of the chassis stand step hanger section of the present invention.

In FIG. 7G, there is shown the stand step hanger section 7290 composed of two upright members 7295 of approximate equal height joined at their respective top surfaces 7300 by a cross member 7305 parallel to the floor plane. The stand step hanger section 7290 is positioned and fixed onto the base section 7000 by each of the two upright members 7295 that are fastened and fixed to each respective inward turned portion 7020 of the side parallel members 7010, 7005, of the base section 7000, showed in FIG. 7B. In this manner, a location is created for receiving hanger boxes 420 and 450 (FIG. 5). All of the fastening and connections of the pieces shown in the FIGS. 7A thru 7G are done with various fastening means known in the art, such as but not limited to, mechanical, screws, pins, bolts, plugs, grooves, adhesive materials, welding etc.

Figure 8A:
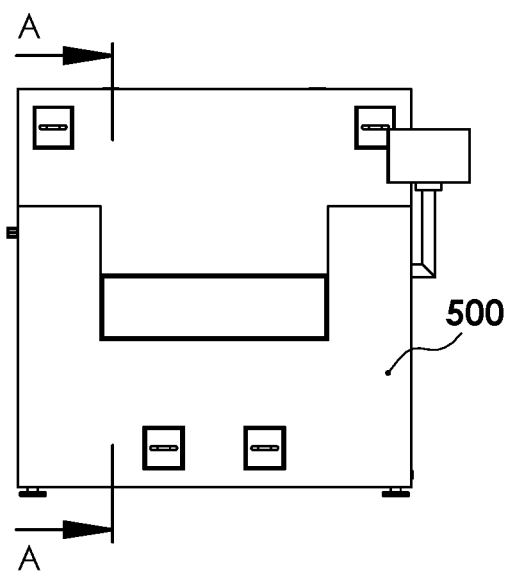
FIG. 8A is an illustration of the frontal view of the present invention with a marked section A-A.
Figure 8B:
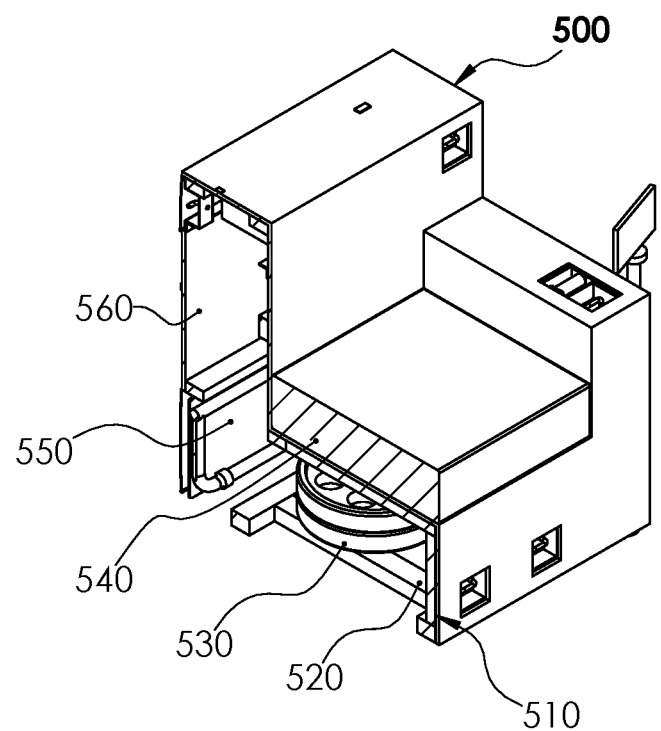
FIG. 8B is an isometric illustration of FIG. 8A in section along line A-A.

FIG. 8A is an illustration in a front view of the chair 500 of the present invention showing a cut along section A-A. FIG. 8B is an isometric illustration of FIG. 8A, showing the view of cut along section A-A of the armchair 500 present invention. The frame 510 shows transversely the weight 530 and its base support 520. Positioned on the armchair is the seat cushion 540 which is made of a resistant material including, but not limited to, special foam, synthetic material, leather, etc. The step-stand 550 is built of a resistant material and stored inside the cavity. The rear section 560 is the back cover of the present invention.

Figure 9A:
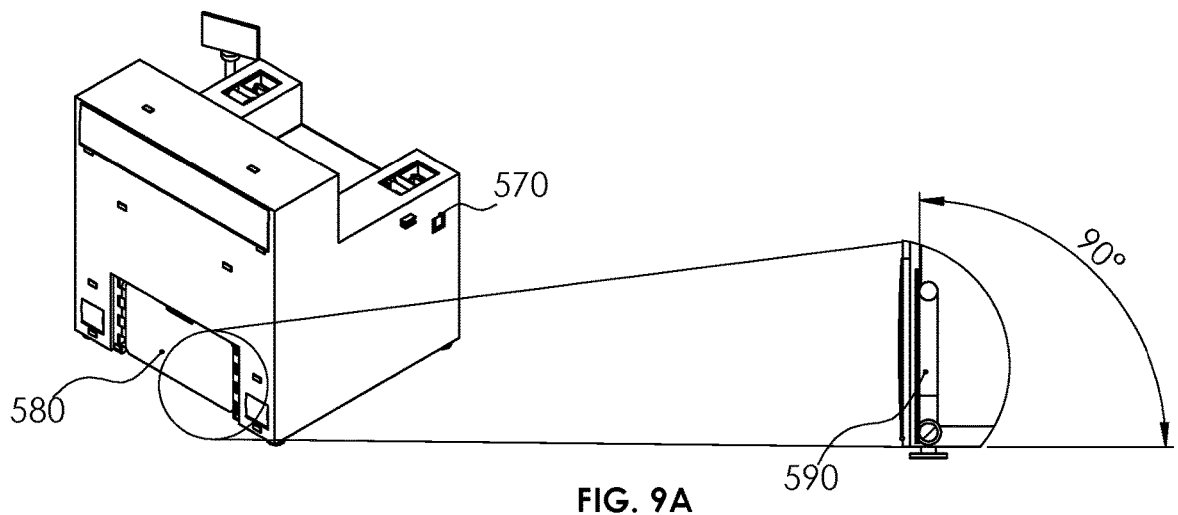
FIG. 9A is a rear isometric illustration of the present invention with the step stand stored at position 0 (90 degrees)

FIG. 9A is an illustration of the step stand 580 in stored first position (position 1). This image shows the step stand 580 stored in the compartment intended for this purpose, and in the lateral view the step stand 580 is stocked at a 90-degree angle to the horizontal. This illustration also shows the right-side computer connector 570 for the computer's bracket.

Figure 9B:
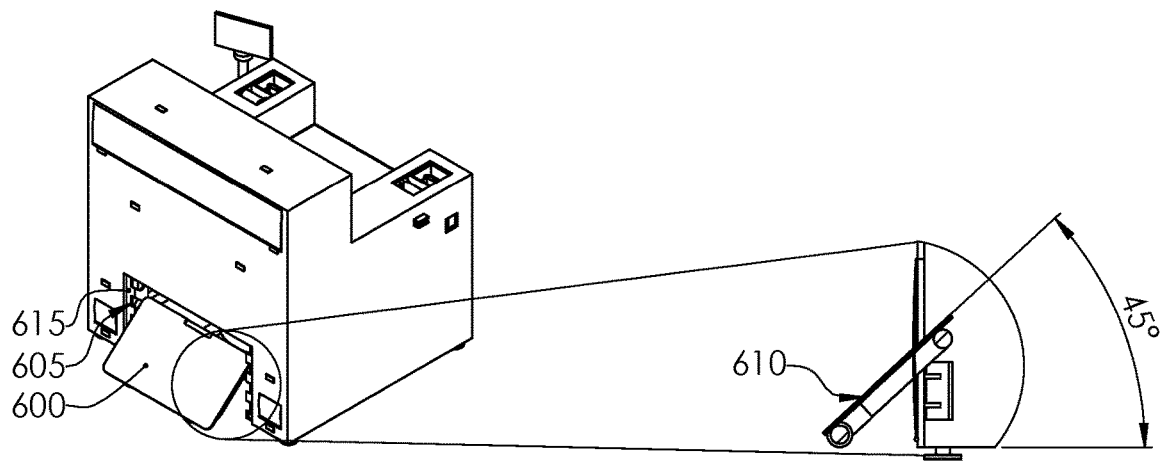
FIG. 9B is a rear isometric illustration of the present invention with the step stand installed at position 1 (45 degrees)
Figure 9C:
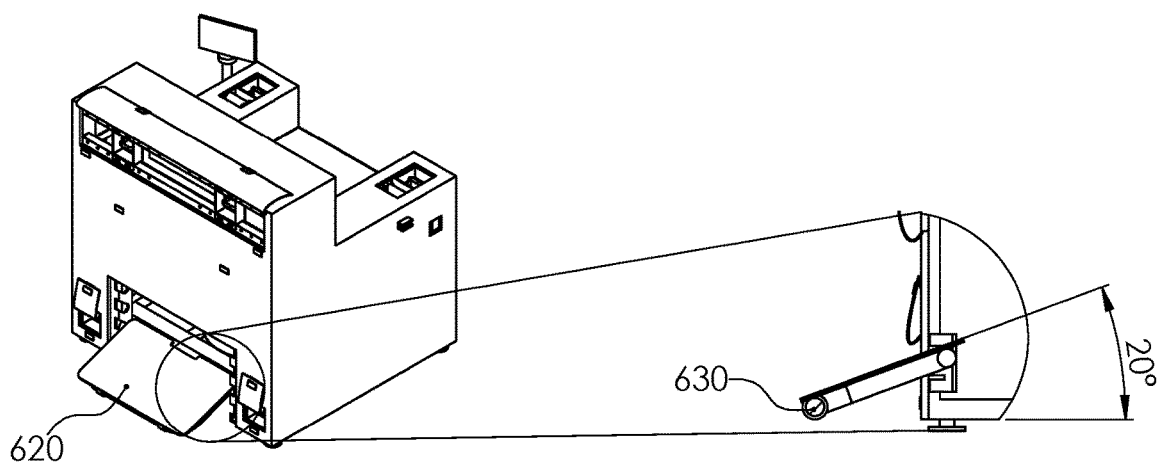
FIG. 9C is a rear isometric illustration of the present invention with the step stand installed at position 2 (20 degrees)

FIG. 9B is an illustration of step stand 600 at a second position (position 2) (45 degrees) from a back view of the present invention. The image shows the step stand 600 located on the second step of multiple steps 605 of the rail support 615. This position 610 provides 45 degrees from the horizontal. The user can stand on this base and stretch the back muscles of the legs or perform other routines. FIG. 9C is the same illustration as FIG. 9B but this shows the step stand 620 at third position (position 3) (20 degrees) 630. Other angles are within the scope of the present invention.

Figure 10:
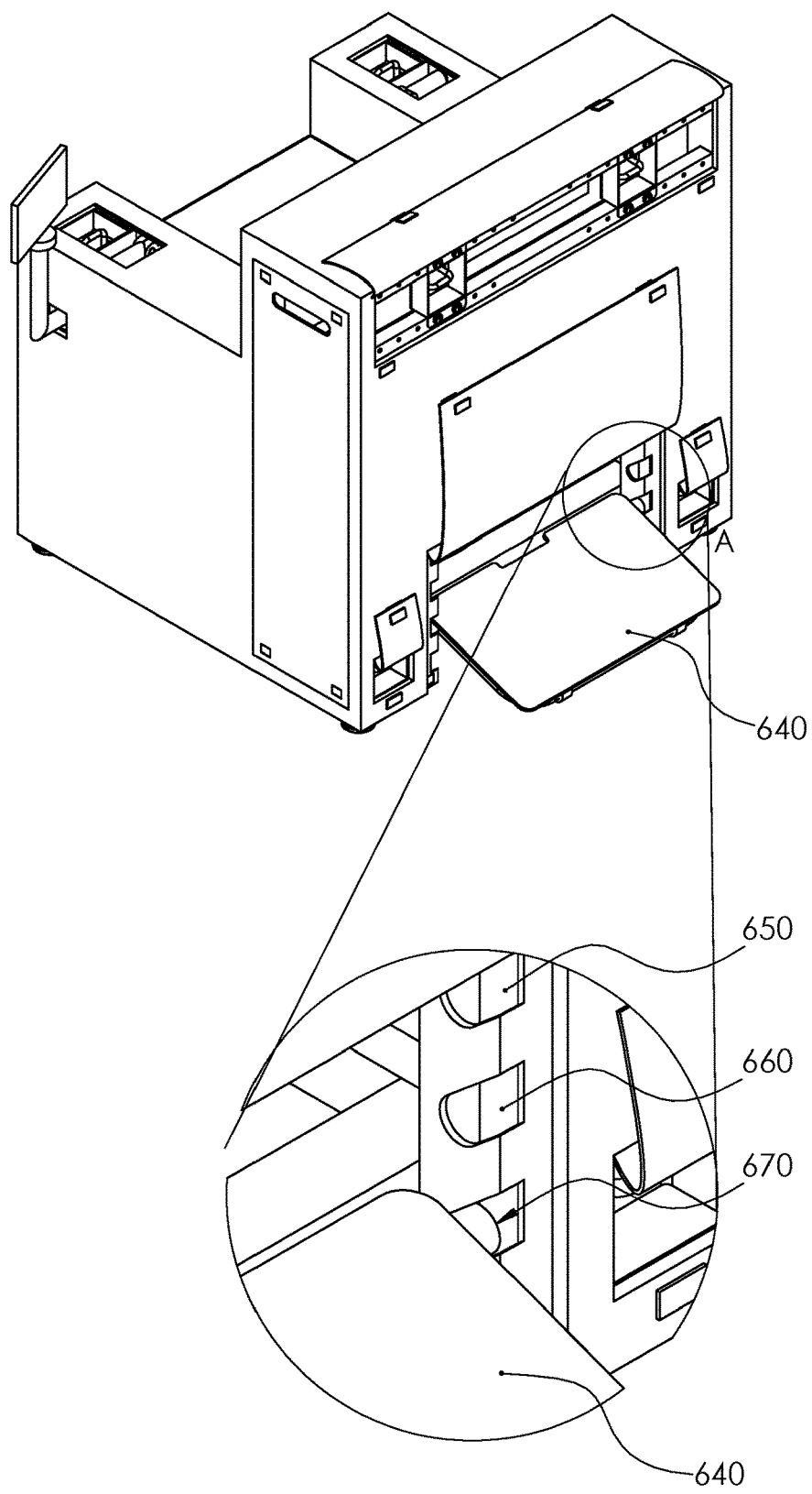
FIG. 10 is a rear isometric illustration of the present invention with the step stand installed at position 2 showing the step stand mechanism.

FIG. 10 is an illustration of the step stand mechanism and its details from rear view of the present invention. In the rear view it is observed how the stand step 640 is supported in one of its three level positions by corresponding slots 650, 660 and 670 to receive the stand step 640 when adjusted to the desired position. By adjusting the positions of the stand step 640, different exercises and exercise levels can be performed.

Figure 11A:
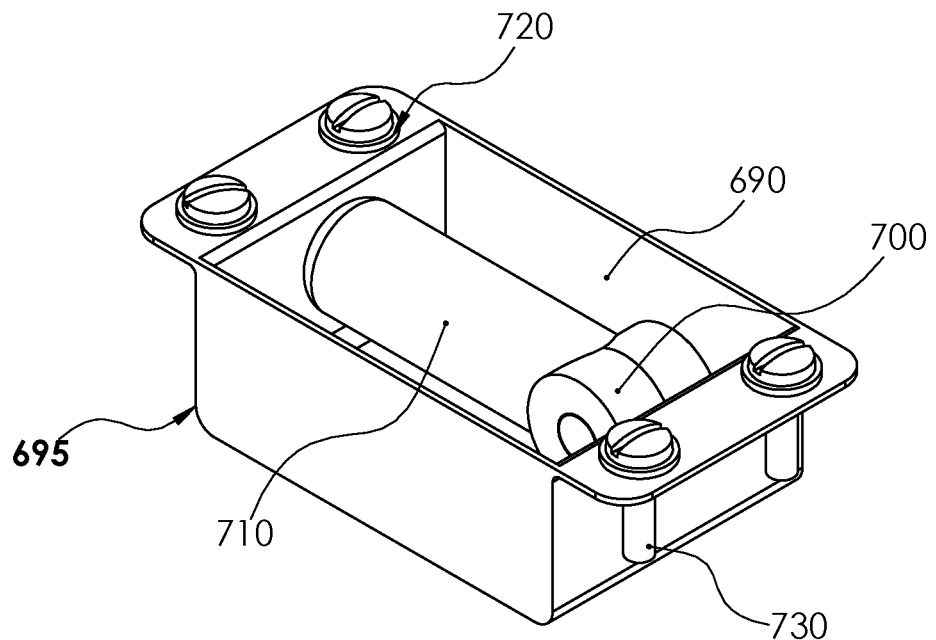
FIG. 11A is an isometric illustration of an armrest handle in closed position.

Referring now to FIG. 11A, is an isometric illustration of the armrest handle assembly 695 in the closed position. The illustration shows the detail of the components that are part of the armrest handle box 690 where the handle 710 is stored while not used. The box 690 is secured to the armchair's chassis by screws 730 and washers 720 that secure the assembly, although other fastening means are within the scope and are acceptable for use. The handle assembly 695 comprises a fixed part 700 and a mobile handle part 710 which can be moved from the closed position to the open position. In this open position, the user can hold the handles to keep the user's back on the backrest of the chair of this invention when the user is doing exercises for their legs (See also FIG. 16C).

Figure 11B:
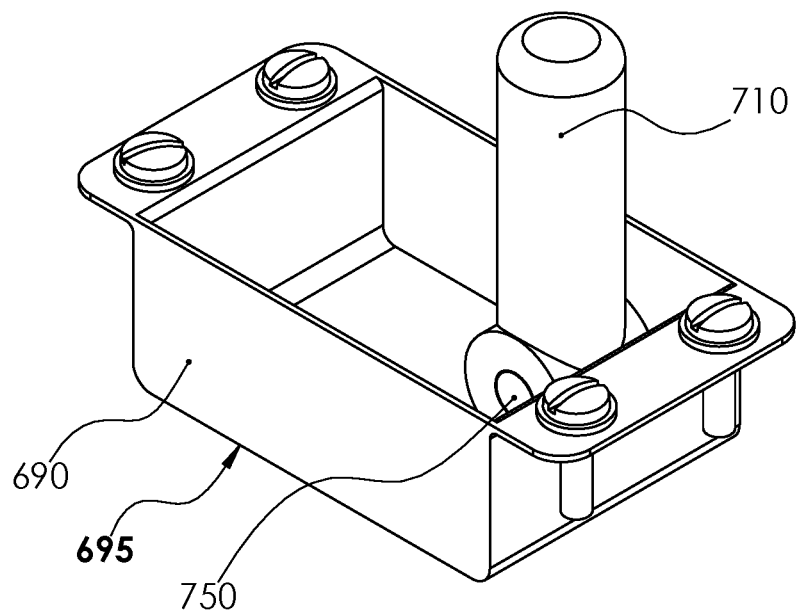
FIG. 11B is an isometric illustration of an armrest handle in open position.

FIG. 11B is an isometric illustration of the armrest handle assembly 695 in the open position of the present invention. The mobile part 710 owes its movement to a pin 750 that is attached to handle box 690 and allows a hinge movement of the handle 710 to reach in a vertical position. When the grip part of the handle 710 is moved up, it remains in an upright position. This allows a user additional support to the armchair while exercising the legs.

Figure 12A:
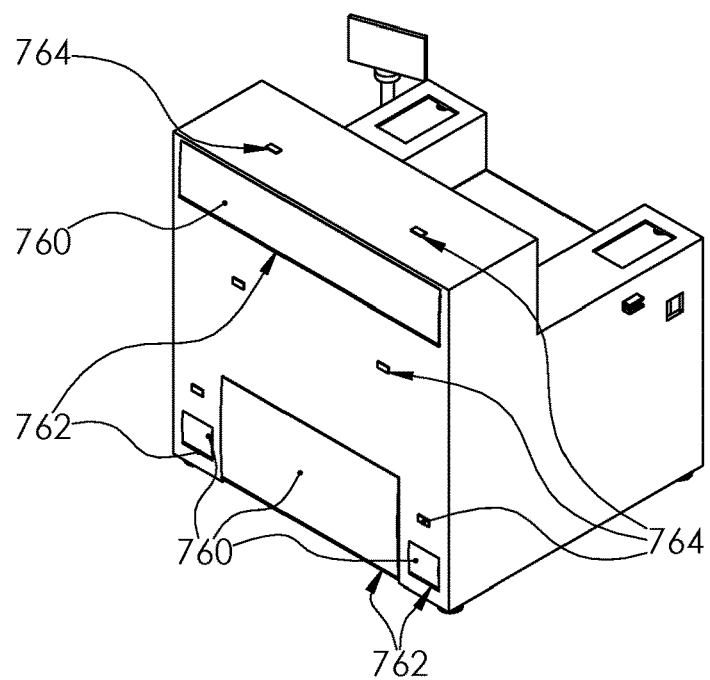
FIG. 12A is a rear isometric illustration of the present invention with all rear flaps closed.

FIG. 12A is an isometric illustration of the rear flaps 760 in closed positions, that is the standard way to maintain the armchair when not in use. The rear view shows the closed back flaps 760, hiding the compartments where hangers are located. These flaps are concealed in order to look aesthetically well presented. The flaps contain a metallic bar 762 that creates weight to keep the flaps straight, firm and well-presented when they are closed. When the flaps 760 are open, they are held by hook and loop type fastener, or similar fastening material 764 to keep the flaps in place.

Figure 12B:
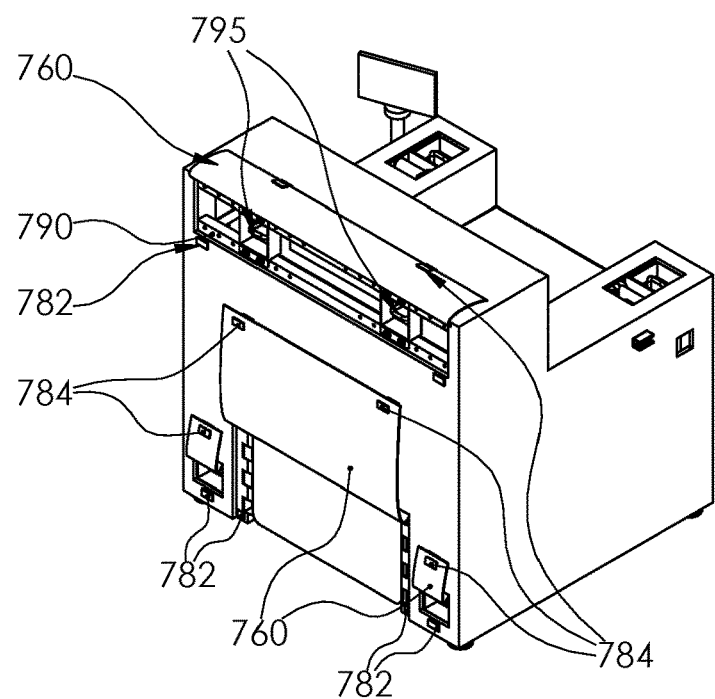
FIG. 12B is a rear isometric illustration of the present invention with all rear flaps open.

FIG. 12B is an isometric illustration of the present invention with the rear flaps opened. The rear view shows the back flaps 760 opened, attached to the armchair in several ways known in the art, including, but not limited to, hook and loop type material 784. Fastening materials 782 are distributed in different sections of the rear rail 790 of the present invention. With the flaps open, the hangers 795 are accessible to the user.

Figure 13A:
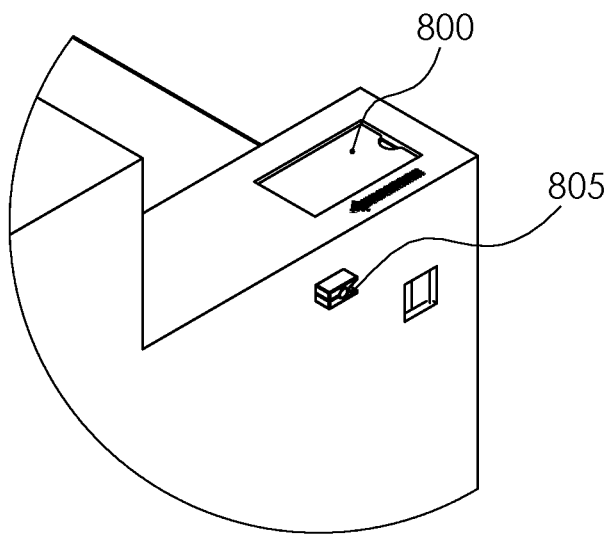
FIG. 13A is an isometric illustration of the right armrest slide flap in closed position.

FIG. 13A is an isometric illustration of the armrest flap 800 in closed position of the present invention on a top surface of the armrest of the chair. The open/close mechanism may include a sliding door, among others. This helps to make the armchair design aesthetical, comfortable and functional when it is in use or not.

Health sensors 805 such as, but not limited to, heart rate, blood pressure, blood oxygen saturation, temperature, among others, are directly installed in the armchair, or with the possibility of connecting by cable or Bluetooth, to measure vital signs and other variables of the user's physical condition, and record them in a database, which may be cloud based.

This health monitoring tool is of great interest to all users, and especially for users who have healthcare limitations to exercise, since the software application (APP) generates early visual and/or oral warnings so that the user stops exercising in case, for example, if the heart rate exceeds a predetermined threshold by the APP or by the user.

Figure 13B:
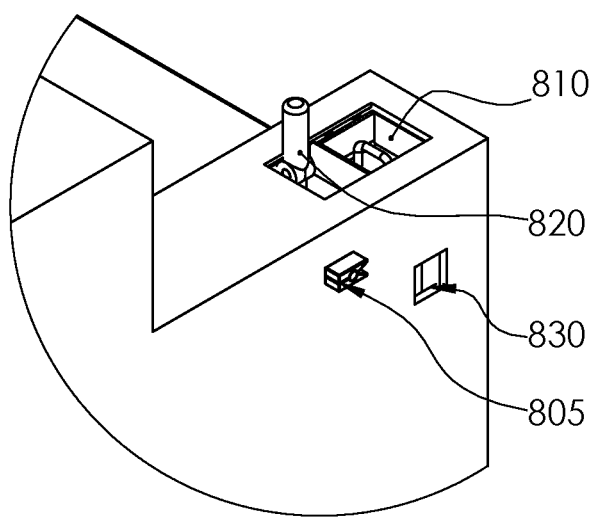
FIG. 13B is an isometric illustration of the right armrest slide flap in open position and showing the place to connect the computer's bracket.

The health sensors can be attached directly to the armchair of this invention as seen in FIG. 13A and FIG. 13B, or can be directly connected to the user's body. Both options transfer data via wireless or wired connection to the computer, including, but not limited to, the following types of health data:

(i) Heart rate (HR), which is a standard vital sign and has become a routine measurement for healthcare; the monitoring of this signal provides information about the status by indicating heart cycle changes.

(ii) Blood pressure (BP), which is a very important cardiopulmonary parameter, indicating the pressure exerted by blood to the arterial wall. BP provides information about the blood flow when the heart is contracting (systole) and relaxing (diastole). It is also an indication of cellular oxygen delivery.

(iii) Respiration rate (RR), which is a fundamental physiologic parameter during observation. Indicators measures distress and potential hypoxia levels.

(iv) Blood oxygen saturation (SpO2), which is a valuable vital parameter and easy to measure using pulse oximetry principles.

(v) Blood glucose (BG), which is a worldwide measurement need in diabetic's treatment. It is important in diabetic global population tracing.

(vi) Body temperature (BT) is the outcome of the balance between heat production and heat loss in the body, being its measurement vital to control high temperatures.

The health sensors can use, but are not limited to, the following interfaces: three leads (positive, negative and neutral), two connections (positive and negative), GLCD connector, USB/mini-USB, serial cable and wireless transmission. Likewise, the step stand in the rear side can include an electronic scale and weight system for the user to keep a historical record of the body weight in the APP.

FIG. 13B is an isometric illustration of the armrest flap in open position of the present invention. This image illustrates the right armrest hanger 810, the right handle 820 located inside the armrests of the chassis (See FIG. 4 and FIG. 5) and the health sensor 805 installed in the right armrest of this invention. The computer's bracket can be connected in the right connector 830 of the present invention.

Figure 14A:
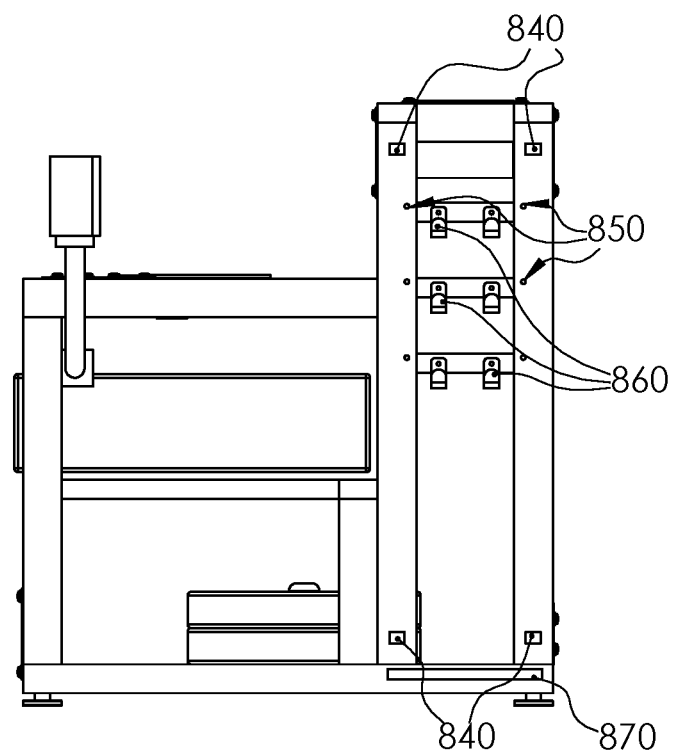
FIG. 14A is an illustration of the left side view and isometric view, showing an optional storage compartment for elastic bands and accessories.
Figure 14A:
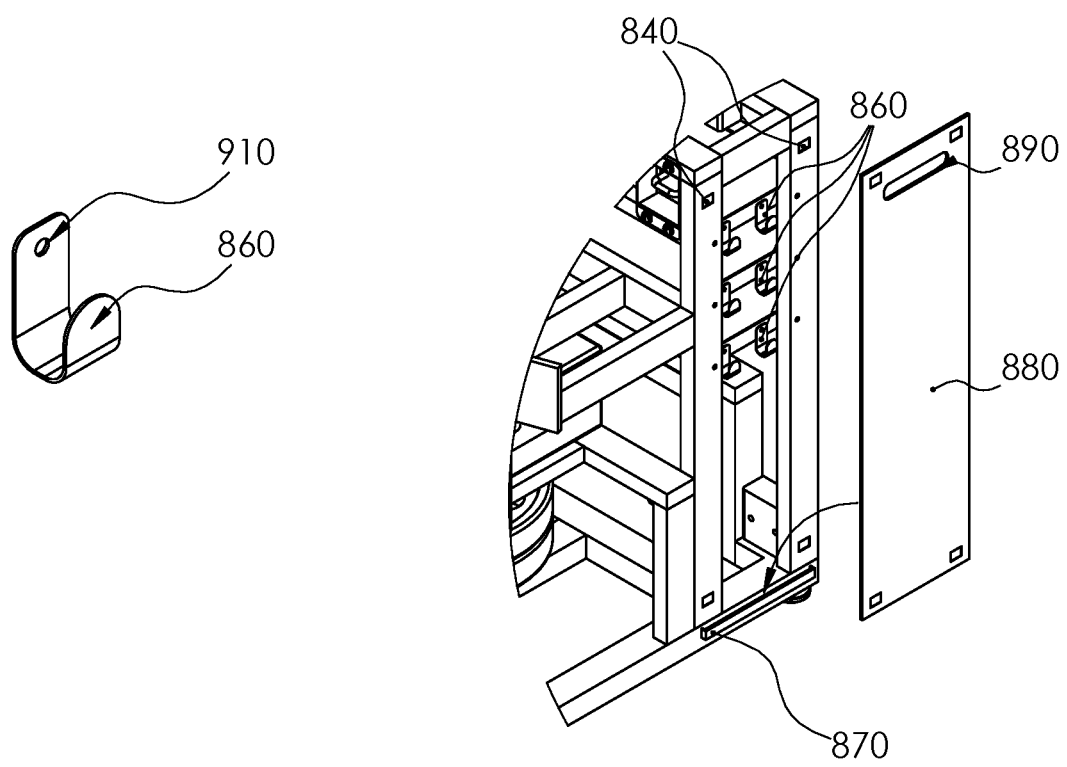

FIG. 14A illustrates a section to store elastic exercise bands and accessories. Access to this area is obtained by removing the side panel rail 880, simply by pulling outward from the slot 890. The side rail is held to the chair at base 870, and adheres to the chair with the assistance of fastening means, such as hooks, hook and loop material, or four magnets 840. When opening the compartment, the user has access to hang the exercise bands and other accessories on the hooks/hangers 860 that can be made of metal or plastic or other materials, and that are attached to the chair by means of a rail and screws 850 or other fastening means. The hooks/hangers 860 have a hole 910 that allows a screw to be attached to an internal rail of the armchair chassis. This type of compartment can be built on each side of the chair, and can cover, without being limited to, additional side, front or rear area of the chair, and even under the cushion seat.

Figure 14B:
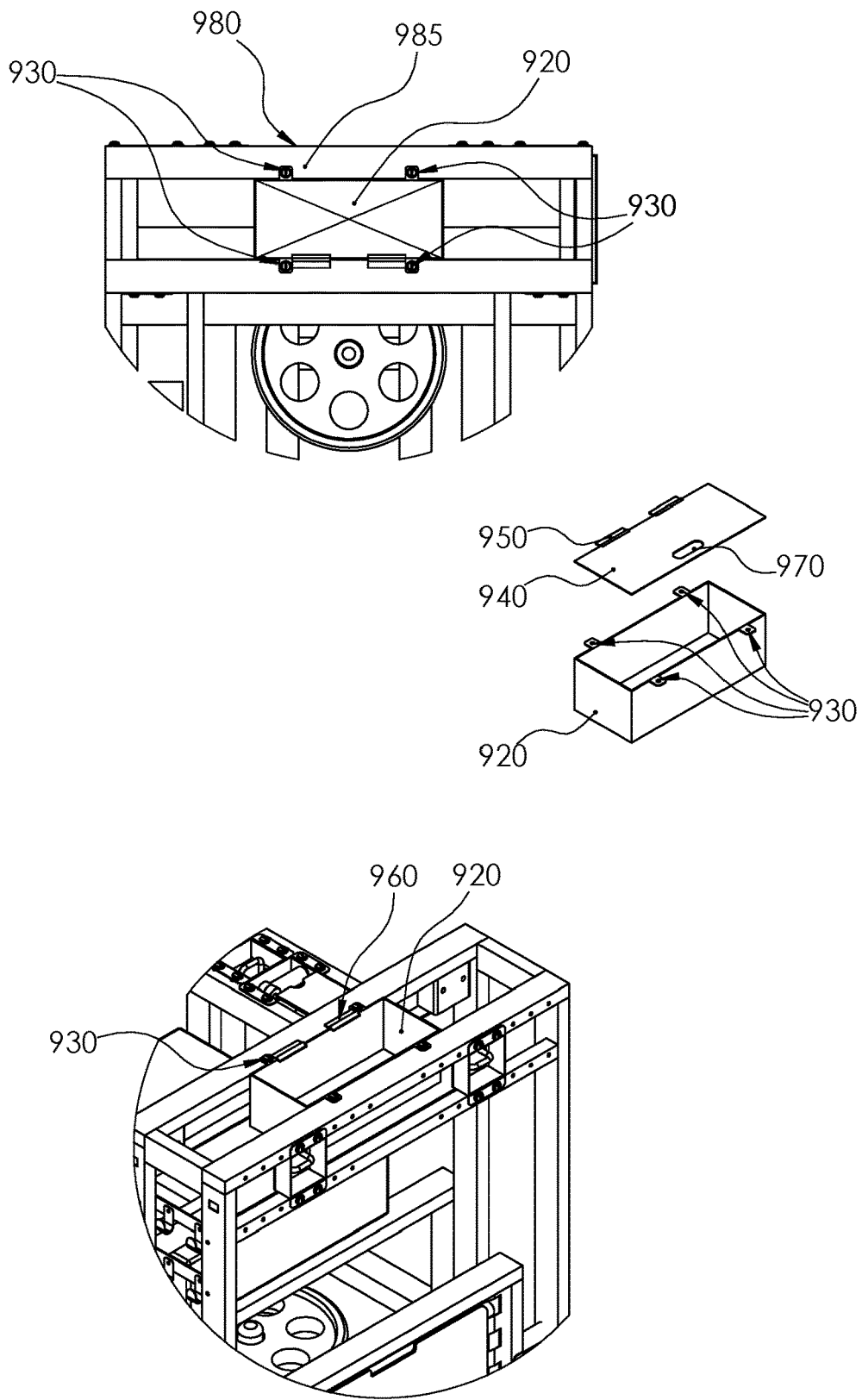
FIG. 14B is an illustration of a top view and isometric view showing another optional storage compartment for elastic bands and accessories.

FIG. 14B illustrates the option of a storing box 920 in the top back rail 985, for storing elastic exercise bands or accessories. The drawer includes holes and screws 930 to attach the storing box 920 to the armchair chassis. It includes a cover 940 with hinges 950 that connect with the armchair hinge receiver 960. The storing box 920 can be opened using the handle 970. The user can have easy access to the box from the back side of the chair 980.

Figure 15A:
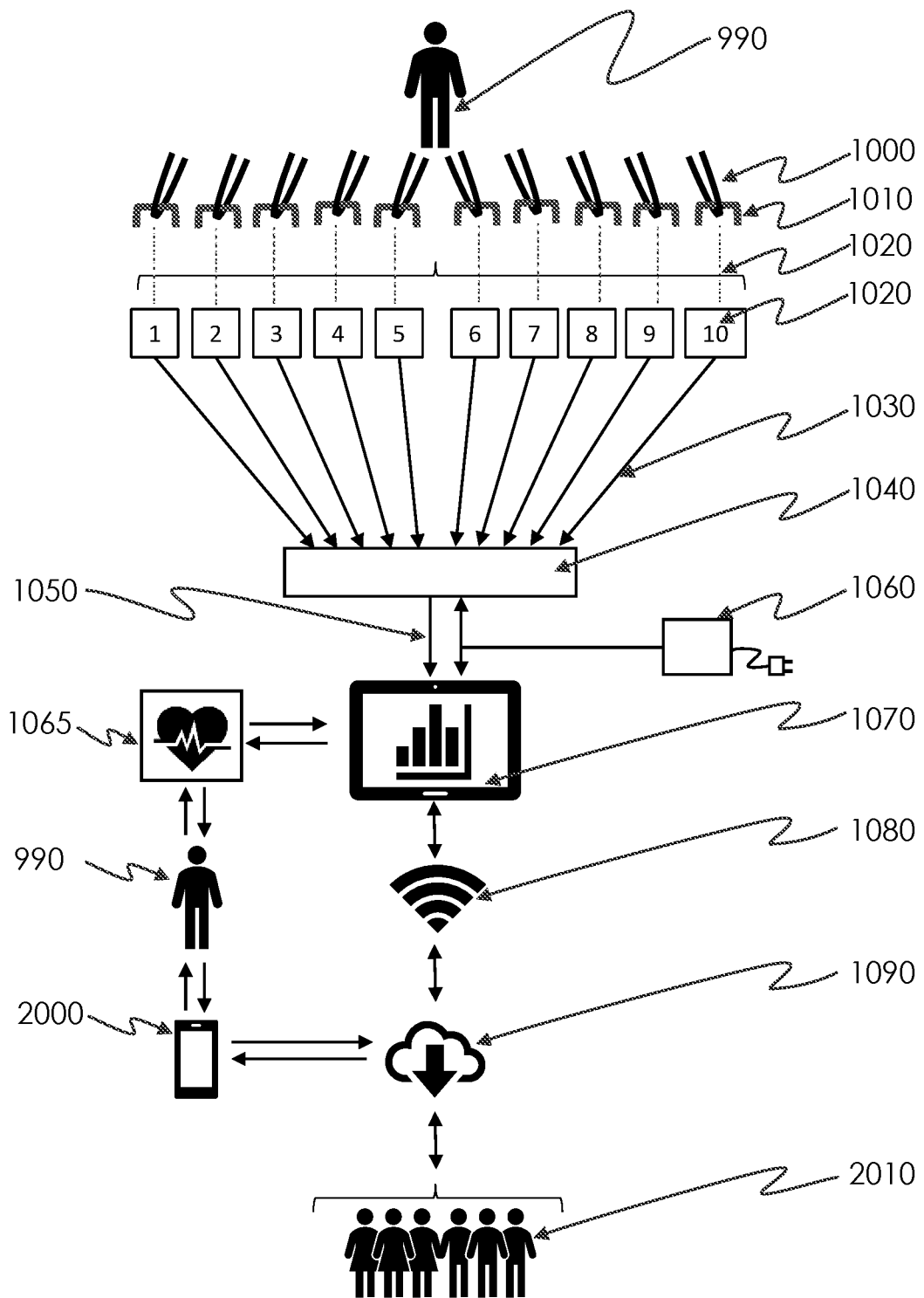
FIG. 15A is an illustration of the connectivity among users with the mechanical, electronic, communication systems and the application software of the present invention.

FIG. 15A is an illustration of the connectivity diagram of the present invention. The user 990 has the ability to attach a plurality of elastic or non-elastic exercise type bands, such as, but not limited to, up to 10 elastic or non-elastic bands 1000 or other materials, to the pressure hangers 1010 as also shown in FIG. 1 Each of these pressure hangers 1010 is wire connected to a respective pressure transducer 1020 that measures the pressure that is made by each exercise band on the respective pressure hanger when in use and at rest. Each pressure transducer 1020 converts this mechanical effort of the user 990 pulling on the bands into a logic signal 1030 that is routed to the input of a multiplexer 1040 where the signals of each transducer 1020 is read. All the input signals of the multiplexer are converted to a single output digital signal 1050 that is sent to a computer or tablet PC 1070. The multiplexor and tablet PC can be externally powered 1060.

The computer or tablet PC 1070 can connect to the internet through its Wi-Fi interface capability 1080. Once connected to the Internet, a software application (APP), included in this invention, establishes communication with a database that is located in a cloud server 1090.

The user has the option to also connect from a mobile device 2000 to access the personal information that is located in the cloud server 1090 with the credentials (username and password). One of the advantages of having the information hosted in a cloud platform is the option, with the previous consent of user, of being guided online by a group of therapists 2010 who provide the user with specialized personnel for therapy or general workout. For guidance on how to perform the exercises, a therapist can monitor user routines and the information recorded in the APP, and with the permission of the user, can activate the camera in the computer to see each other and, allowing the therapist or doctor to provide the user with guidance and professional consulting.

Figure 15B:
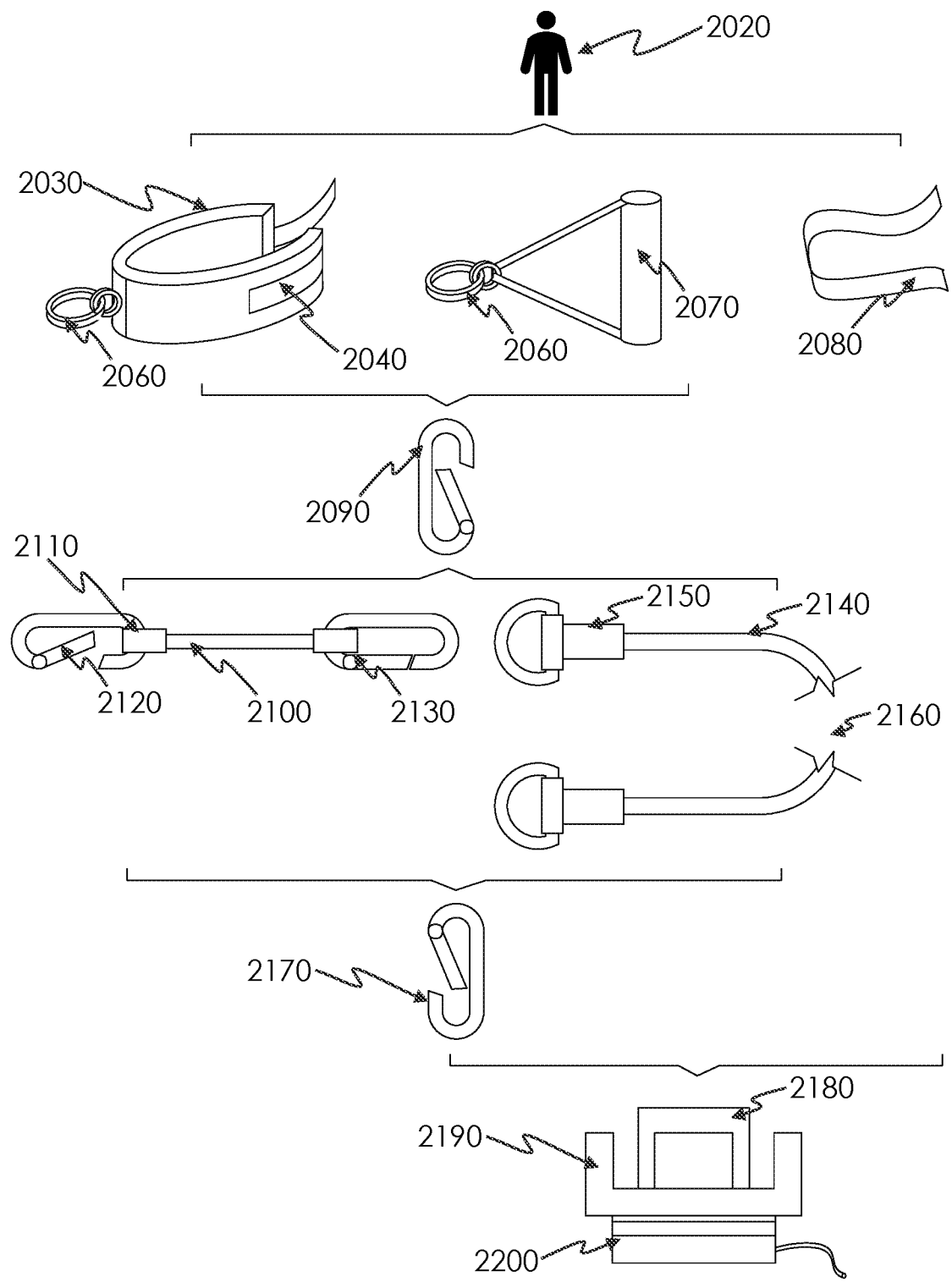
FIG. 15B is an illustration of the mechanical connection of the elastic bands system with the user and armchair of the present invention.

FIG. 15B is an illustration of how a user could use rubber resistance or elastic bands of different resistance, or other types of elastic or non-elastic fasteners and accessories and perform workout with the armchair of the present invention.

The user 2020 may choose to use different types of fasteners to attach to the bands system, for example, but not limited to, ankle straps 2030 for feet, that have hook and loop type fastener 2040 and a metal ring or similar 2060. For hands, the user could use handle fasteners with a comfortable grip 2070 that has a metal ring 2060, among other different options currently commercially available. Then, the user can connect these fasteners 2030 and/or 2070, to other accessories, such as to resistance elastic tubes 2100 with hooks 2130, which have a fixed position 2110 and a mobile part 2120 to open or close access to other fasteners; to resistance elastic tubes 2140 or bands 2160, elastic or non-elastic, with metal or other rigid material rings 2150 installed at their ends. Elastic bands or any other elastic or non-elastic material can use a fastener 2170 to connect to pressure hangers 2180 of the armchair that are located in pressure boxes 2190 with pressure transducers 2200. These pressure transducers 2200 send the pressure signals to the multiplexer creating an output signal and this output signal to the computer as explained in FIG. 15A. The user can also use and attach the elastic bands 2080 directly to the pressure hangers 2180 of the armchair of this invention.

Figure 16A:
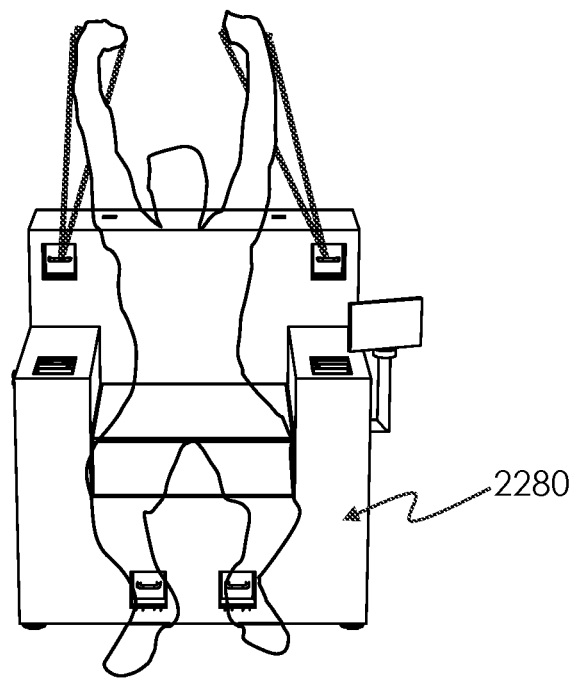
FIG. 16A is an illustration of a user sitting and exercising using the backrest hangers of the present invention.

FIG. 16A is an illustration of how a seated user could use the present invention to do therapy or workout for the shoulders, arms, chest, waist, abdomen, among other areas, by connecting the bands system to the backrest pressure hangers 2180 (FIGS. 1, 150 and 160) of the armchair 2280 of the present invention. The pressure signals of both sensors are transmitted to the computer. The APP may visually and/or orally inform the user of the number of repetitions, the pressure in pounds (or other metrics) in each band or on average, the next recommended exercise, early warnings, recommendations about changing the strength (color or length of the band) of the band, etc. In case of a guided online therapy session, the therapist will have access, with permission of the user, to see the statics of the workout and provide advisory to the user. All information can be recorded in the cloud-based servers and the APP can provide statics to the user and/or therapist to improve the user's recovery from injuries, healthcare conditions or just to stay in good shape and healthy.

Figure 16B:
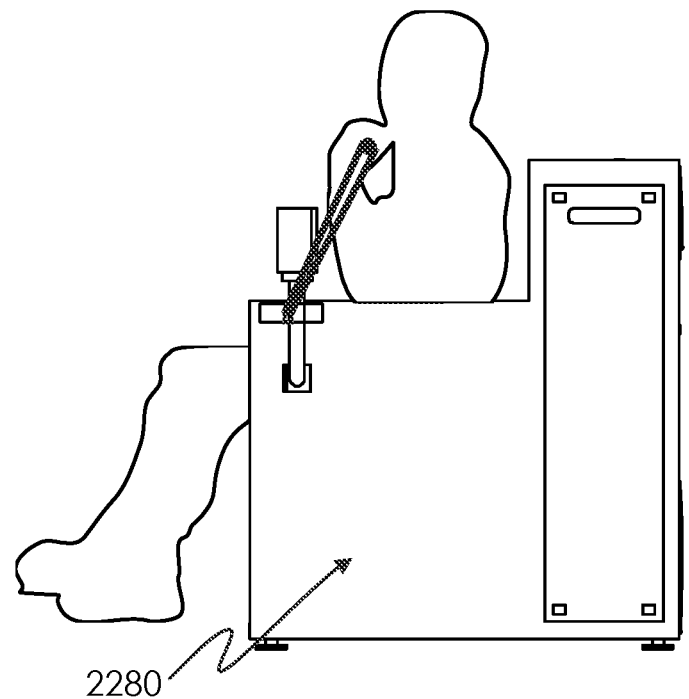
FIG. 16B is an illustration of a user sitting and exercising using the armrests hangers of the present invention.

FIG. 16B is an illustration of how a seated user does therapy or workout for the upper arms, forearms, elbows, shoulder, back, among other areas, by connecting the bands system to the armrest pressure hangers 2180 (See also FIGS. 1, 130 and 165) of the armchair 2280 of the present invention.

Figure 16C:
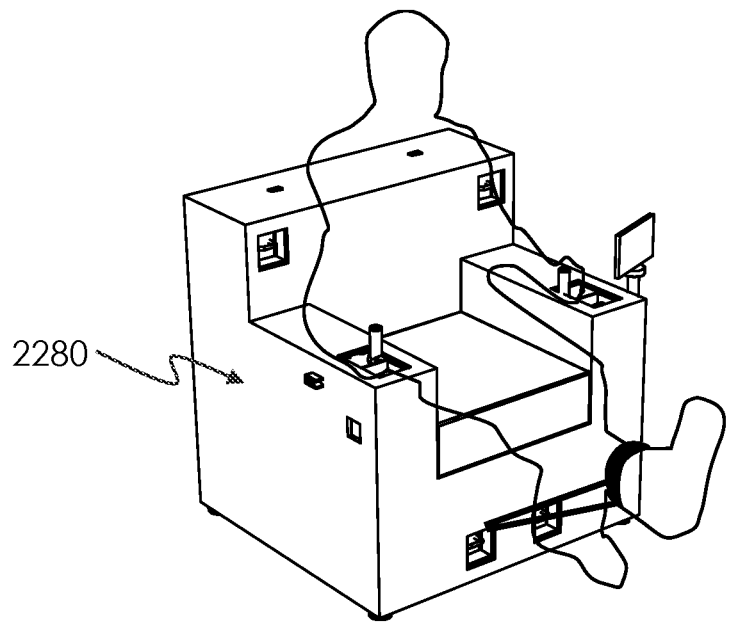
FIG. 16C is an illustration of a user sitting and exercising using the lower front hangers of the present invention, holding the armrest handles with hands.

FIG. 16C is an illustration of how a seated user could do therapy or workout for the thighs, knees and calf, among other areas, by connecting the bands system to the lower front pressure hangers (See also FIGS. 1, 110 and 120) of the armchair 2280 of the present invention. In this position the user can hold the handles to keep the back on the backrest of the chair of this invention.

Figure 16D:
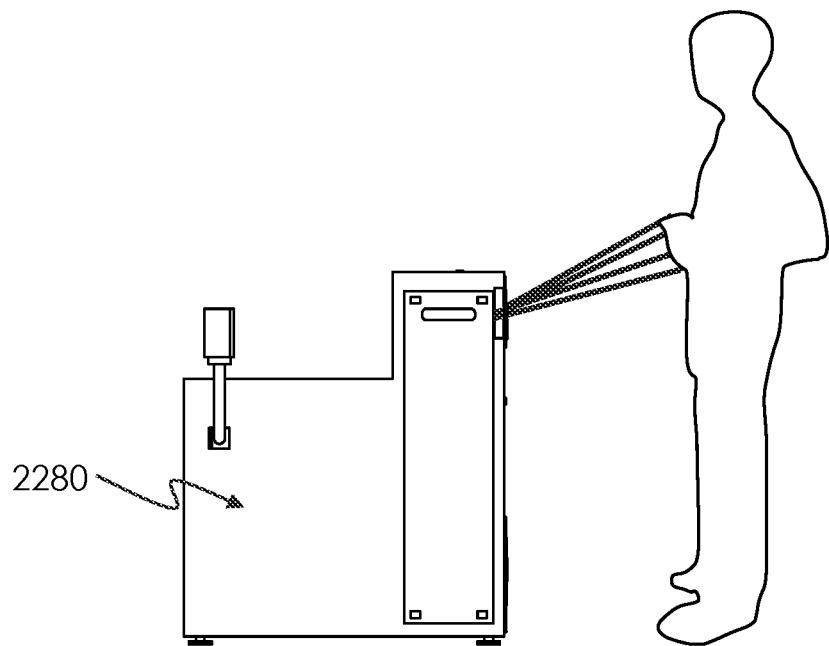
FIG. 16D is an illustration of a user standing and exercising using the upper back hangers of the present invention.

FIG. 16D is an illustration of how a standing user could do therapy or workout for the back, arms, forearms, shoulder blade, abdomen, armpit, breast, among other areas, by connecting the bands system to the rear upper pressure hangers (See FIG. 5, 400) of the armchair 2280 of the present invention.

Figure 16E:
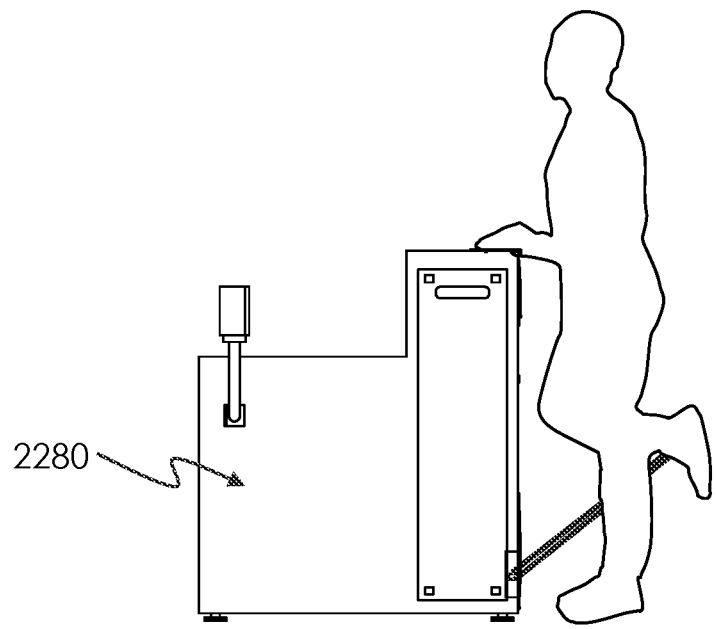
FIG. 16E is an illustration of a user standing and exercising using the lower back hangers of the present invention.

FIG. 16E is an illustration of how a standing user could do therapy or workout for the back, buttocks, thighs, legs, among other areas, by connecting the bands system to a rear lower pressure hanger 2180 (See also FIGS. 5, 450 and 420) of the armchair 2280 in the present invention.

Figure 16F:
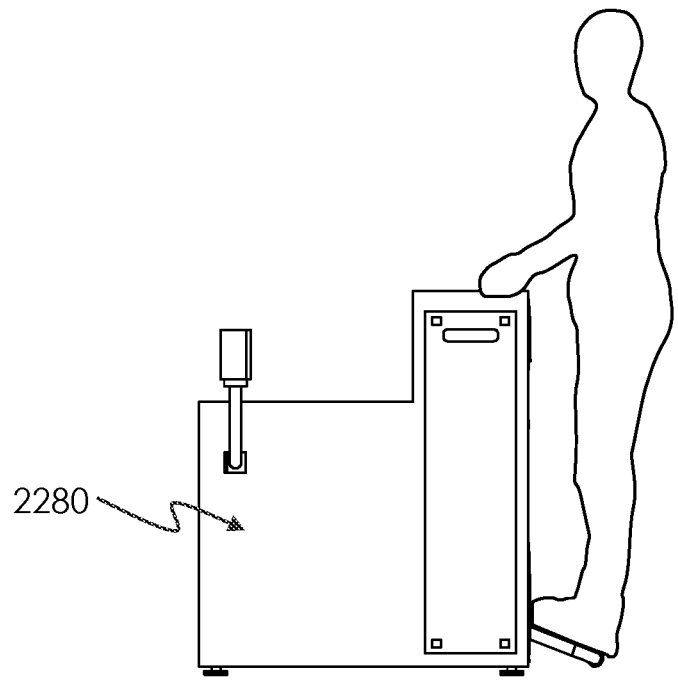
FIG. 16F is an illustration of a user standing on the step stand stretching the back muscles of the legs.

FIG. 16F is an illustration of how a standing user could use the stand step 640 (see FIG. 10) included in the armchair 2280 of the present invention, to stretch calf, thighs and other muscles for therapy purposes or after finishing the workout.

Figure 17:
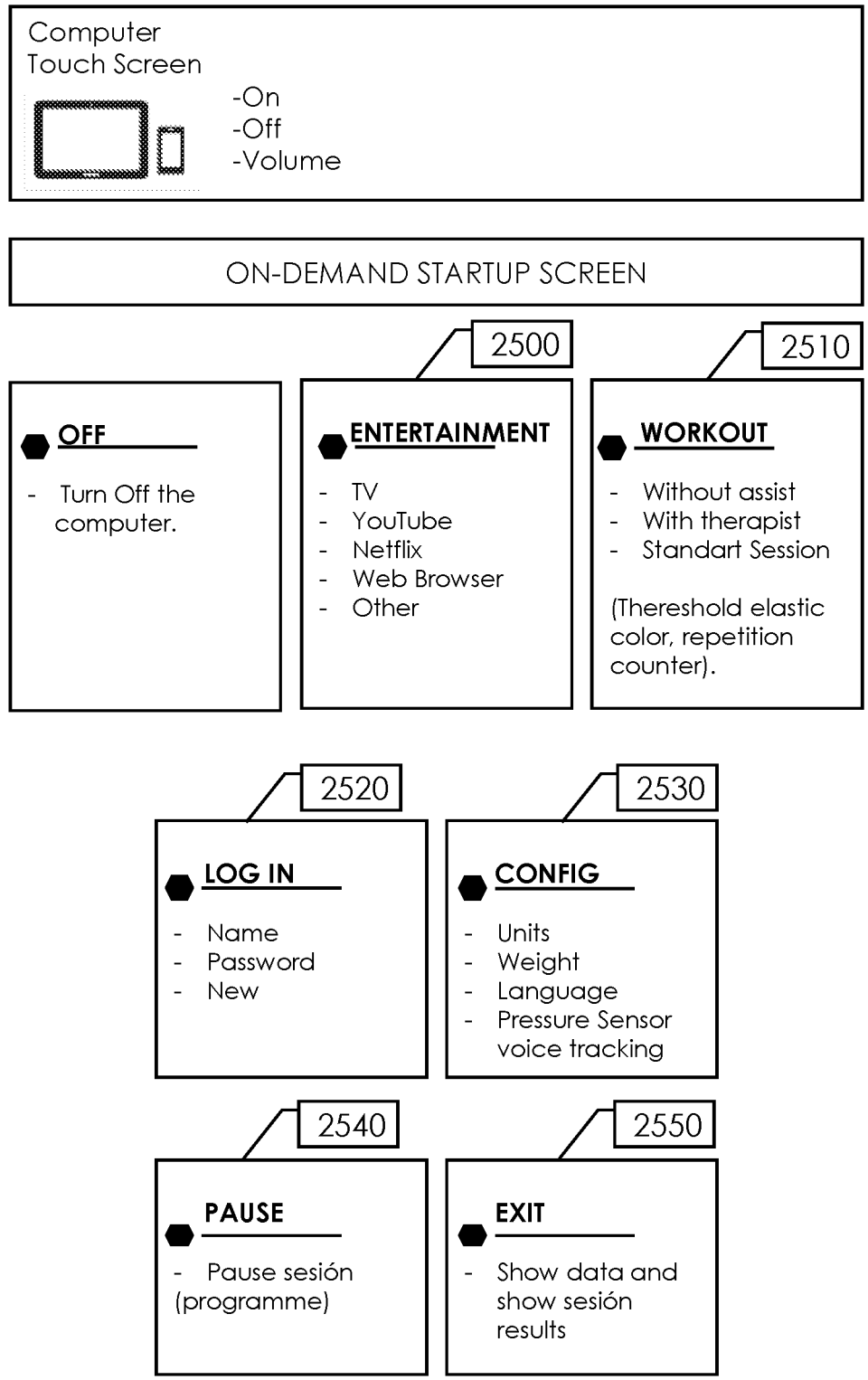
FIG. 17 is an illustration of the start-up Screen of the software application (APP) that is included with the armchair of this invention.

FIG. 17 is an illustration of the Start-Up Screen of the software application (APP) that is included with the armchair of this invention or that can be downloaded from the cloud. The image shows the start interface that is presented to the user in order to interact with the present invention. The computer may be a 10 inch touchscreen tablet console, among other possible sizes and types, that provides the user with a complete interactive experience with advanced connectivity. Different options are provided to the user in the Start-Up Screen including, but not limited to, Entertainment 2500, Workout 2510, Log In 2520, Configuration 2530, Pause 2540 and Exit 2550 touch-screen keys. The computer comes with the basic options to turn on, off and volume control. Power supply and data transfer cable coming from the voltage adapter and multiplexor, respectively, are wired through the bracket to the computer.

Figure 18:
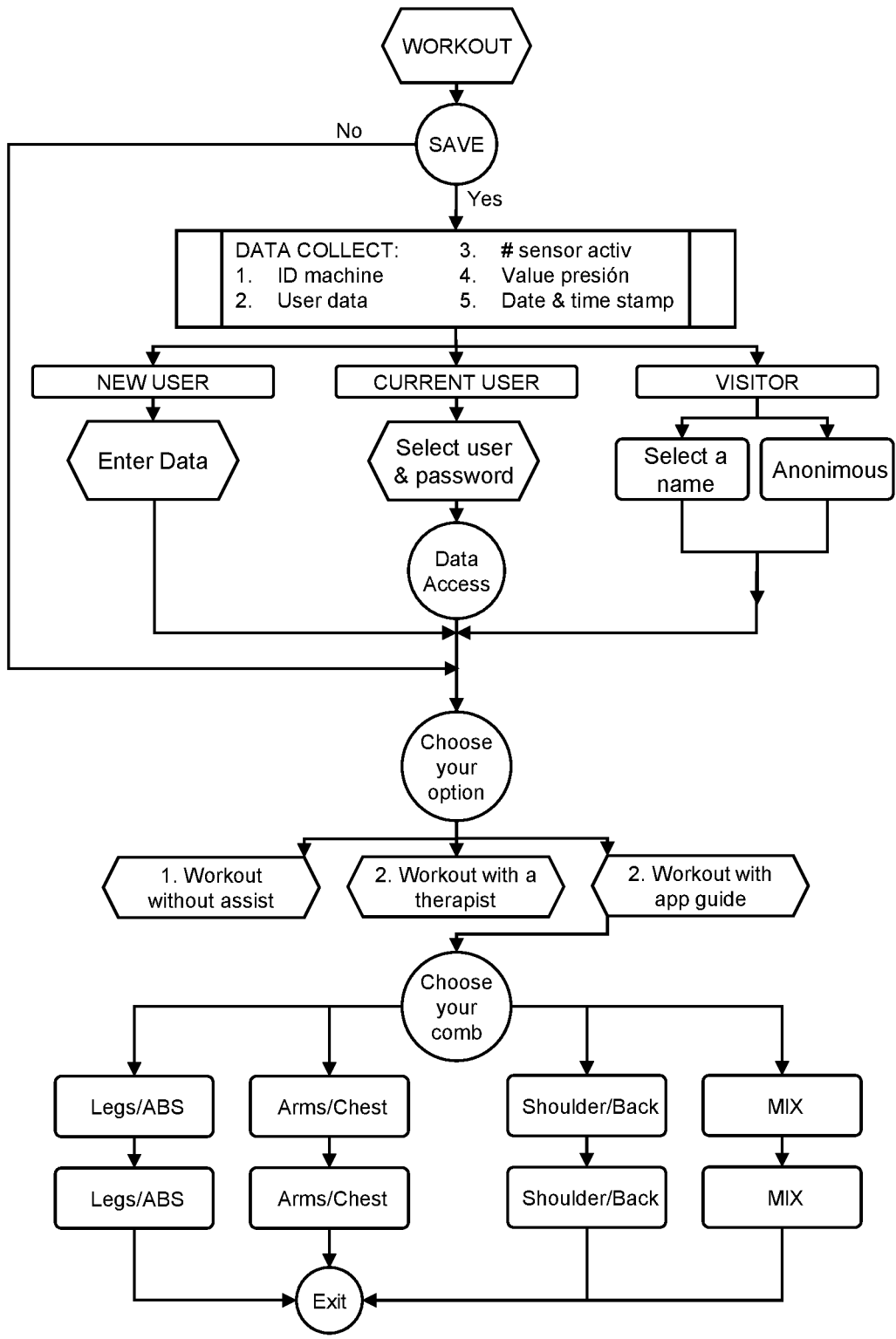
FIG. 18 is an illustration of the flowchart of the software application (APP) that is included with the armchair of this invention.

FIG. 18 is an illustration of the flowchart minimum features that are included in the software application (APP) that is provided with the armchair of this invention. The user can also download the APP from the cloud to a smart phone. The user interface for workout module presents a series of steps to follow where the user is guided through each of the options offered by the interface.

As a first step, the user is asked to indicate if he/she wants to save the workout data. The user has two options: (i) to save the workout session data including, but not limited to, user identification, repetitions counter, pressure value vs sensor identification, date and time stamp for each data collected, online therapy session record, or (ii) not to save the workout session. Once the user has chosen from the options (i) or (ii) above, the user interface presents three options: "new user", "current user" or "visitor". The "new user" option guides the user to store all their personal information including, but not limited to, name, age, height, weight, health condition, username and password. The "current user" option asks the user to enter the Log-In information (name and password). In case the user has forgotten the password, he/she can request the APP to send a message to the contact email provided by the user while creating the account, giving instructions to reset the password in order to gain access to the saved data. Once the Log-In procedure is successful, the system loads the information regarding the registered user. The "visitor" option will allow the user to execute a routine just by entering a name or even without it.

After one of the 3 above mentioned options is chosen, the interface will present 3 options to the user: "Workout without assistance", "Workout with an online therapist assistance" or "Workout with an application guide". For the "Workout without assistance" option, the user will work freely using all the available accessories and features of the present invention. The APP will save the information if the user has chosen that option. For "Workout with an online therapist assistance", the user will have the possibility via the APP to come into contact with a pre-registered therapist who can provide specialized assistance in real-time for the execution of customized routines, for instance for recovery from an injury, for training, etc. This type of service will be provided to members who have access to online payments. The "Workout with an application guide" option allows the user to work under a routine guided by the preconfigured training system. This option includes, but is not limited to, 4 types of sessions such as legs/abs, arms/chest, shoulder/back and mix options.

These routines are the standard routines. The mix option is a series of exercises that involves some or all of the six areas of the body previously described, and which are designed by qualified therapists or trainers in this type of routines. The APP provides the option to the user to show which sensor(s) of the armchair is (are) being used, provide a visual and/or oral information about the pressure value, the number of repetitions, exercise recommendations, among other information.

IoT Capabilities of the Therapy Armchair:

The therapy armchair of this invention can include, but not limited to, a software application (APP) to help users to use and enjoy the time during exercises. Some of the information and features found in the APP include, but are not limited to: User Profile; Location; Recommended exercises; pressure measures; repetition counter; History Data and Statistics; Session Upload/Download to/from the Cloud; Download Videos or Music; TV/Internet options; Contact online a Specialist; Print a Report; Send a Report by email; System Configuration.

Different kinds of sensors including, but not limited to, pressure transducers, pulse and oxygen sensors, other healthcare sensors can be installed in the therapy chair of this invention, allowing the exchange of data with other IoT apparatuses, software, databases, etc. The data reaches a database where it is analysed and presented using Data Science algorithms programmed in an AI machine. IoT (Internet of things) is a technical name for any technology that captures data from any device or subject and using an available network transmits it to a database for analysis.

The therapy armchair of this invention can capture health data, muscular strength, early warnings, security alerts or any other information in a home, public or office environment which it can measure using an array of sensors. Then, the therapy armchair transmits the data using the computer as a modem connected to the internet via a wired (LAN) connector or a Wireless (Wifi, Bluetooth, 3G, 4G, 5G) transport protocol. The data reaches a database where it is analysed using data Science algorithms programmed in an AI machine. The APP allows the user to set the maximum values that it is desired not to exceed, as well as the incremental/decremental rate of some of the variables, for example, the Heart Rate, among other programmable functions, and generate a visual and/or audio early warnings and security alerts during the usage of the armchair of this invention, as well as optionally sending messages via the internet to the User's contacts in such a way that the message of a potential health risk of the user reaches other people who can help, including, without limitation, contacting 911, emergency services or other help centers of a medical nature.

Usage Options of the IoT Therapy Armchair

There are different kind of uses for the IoT therapy armchair of this invention including, but not limited to, the following: 1. At home for a family member who needs to recover from a body injury by doing continuous therapy sessions, and, in general, for all family members to do workout just to stay in good shape and healthy. Similarly, for those sedentary or lazy members who generally do not want or do not have time to do exercise inside or outside home; 2. Hospitals may be interested based on the type of patients served. For example, cancer hospitals may find it beneficial for a subpopulation of clients; 3. Retirement homes and assisted living facilities; 4. Stay at home parents- to stay active while kids play; 5. Busy family members/professionals/college students that may not have the time to go to the gym or outdoors for exercise; 6. Insurance companies who are interested in saving money by financing online therapy sessions for long and mid-term injured clients; 7. The progressive bands system jointly with the armchair of this invention could hit the major UE/LE (upper extremities/lower extremities) muscle groups for all people.

Description of Production

The armchair chassis of this invention is produced of a heavy-duty resistant material that can support the strengths done by the user and bands system. This chassis is, but not limited to, of steel, stainless steel, iron, wood, etc. If the heavy-duty chassis is metal, a welded frame provides a stronger resistance and durability. It should be noted that the research and development of new materials that can be used in its manufacture leaves an open amount of possibilities on the table that will be evaluated and tested in the laboratory to find the best materials that adapt to the main suppliers to the design of this invention.

Stability refers to the stability of the armchair, this determines that the chair does not tip over (some of the legs lose contact with the floor) when the user, for example, is preparing to do a physical exercise standing or well using the step-stand that is in the back.

The overall stability is affected by the position of the combined center of gravity of the user and the chair in relation to its base. One way to increase overall stability is with the location of the mobile weights that have been detailed in the previous points.

The armchair cushion, backrest, and armrest are used for three reasons: comfort, pressure relief, and postural support. Therefore, its design is very important as it will help users to use the armchair for much longer when it is about exercising in a sitting position. Seat cushion and armrest will be produced of a material that provides comfort when the armchair is used just to relax, but at the same time, the material should provide an elasticity recovery feature after pushing it in any direction, providing a long-term use of the armchair of this invention.

The pressure transducers, wiring, transmission protocols and else will comply with the local standards for use in each country or geographic region.

The invention is not restricted to the details of the foregoing embodiments. The invention extends to any novel one, or any novel combination, of the features disclosed in this specification (including any accompanying claims, abstract and drawings), or to any novel one, or any novel combination, of the steps of any method or process so disclosed.

What is claimed is:

1. An armchair for therapy, comprising:
   an armchair chassis having a back section, a pair of side sections connected to said back section with an armrest on a top surface of each side section; said back section and pair of sides defining a seating area; a front leg support section extending downward from and below said seating area and connecting each of said side sections;
   a plurality of pressure hangers fastened to said chassis, each of said plurality of pressure hangers capable of receiving an exercise accessory;
   each of said plurality of pressure hangers connected to a respective pressure transducer, said respective pressure transducer measuring an amount of pressure applied to each of said plurality of pressure hangers;

said pressure transducer converting said amount of pressure applied to each of said plurality of pressure hangers into a logic signal;

said logic signal routed to a multiplexer to read the logic signal of each of said plurality of pressure hangers;

said multiplexer converting all of said logic signals to a single output signal;

said single output signal communicated to a computing device.

2. The armchair for therapy according to claim 1, further comprising weight located in said armchair to provide stability when a user does therapy in a standing position.

3. The armchair for therapy according to claim 1, further comprising an elastic bands system for said exercise accessory.

4. The armchair for therapy according to claim 1, further comprising healthcare measuring sensors.

5. The armchair for therapy according to claim 1, further comprising an application on said computing device that communicates online and provides interactive therapy guidance.

6. The armchair for therapy according to claim 1, wherein said armchair chassis further includes a base section with a weight support section connected to said base section, a seat member section connected to said base section, a first and second arm rest sections connected to said base section, and a backrest section connected to said base section.

7. The armchair for therapy according to claim 6, wherein said base section is a U-shaped piece having a pair of parallel side members connected by a front member between said pair of parallel side members; each of said pair of parallel side members having an inward turned portion at an open end of said U-shaped piece, said inward turned portion creating a corner to align with said backrest section; and a cross support member fixed between said pair of parallel side members.

8. The armchair for therapy according to claim 7, wherein said base section includes a weight support section, having an H-shaped frame piece with two parallel members and a cross member located between and connecting said two parallel members; a guide pin for receiving weights extending upward from said cross member; said weight support member piece fixed inside said base section between said front member and said cross support member of said base section.

9. The armchair for therapy according to claim 7, wherein said seat member section has a front, a back and four vertical pieces of equal height; two of said vertical pieces located in said front of said seat member section and two of said vertical pieces located in said back of said seat member section; said front two of said vertical pieces secured by a cross beam and each of said two front vertical pieces fixed to a first and a second seat inner beam;

said back two of said vertical pieces connected by a seat back beam piece;

each of said first and second seat inner beams connected to said seat back beam piece;

said seatback beam piece longer than said cross beam piece securing said front two of said vertical pieces;

said two front vertical pieces of said seat member section are positioned and fixed along a top surface of said front member of said base section, and said two vertical back pieces are positioned and fixed to the parallel side members of said base section.

10. The armchair for therapy of claim 7 wherein said first and second arm rest sections are an L-shaped right angle piece; said first and second arm rest sections each have a pair of vertical and parallel members, said vertical and parallel members are positioned on said front member of said base section; said vertical and parallel members each intersect and connect with a top pair of parallel members parallel to said base section; said top pair of parallel members having a cross spacer piece fixed between said top pair of parallel members at a front end of each of said top pair of parallel members.

11. The armchair for therapy of claim 10 wherein said backrest section has two upright parallel members on a right side and two upright parallel members on a left side; a first cross member positioned between said two upright parallel members on said right side and a second cross member positioned between said two upright parallel members on said left side;

a pair of top members perpendicular to said two upright parallel members on said right side and perpendicular to said two upright members on said left side; said pair of top members connected to a top end of each of said four upright parallel members;

said four upright parallel members fastened on the base section parallel side members with the back two upright parallel members aligned with said back corners of said base section;

said backrest section having a cross beam fixed between two front upright parallel members; said first arm rest section and said second arm rest section connected to said cross beam to secure said first arm rest section and said second arm rest section to said backrest section.

* * * * *